US00RE44022E

(19) United States
(12) Reissued Patent
Betz et al.

(10) Patent Number: US RE44,022 E
(45) Date of Reissued Patent: Feb. 19, 2013

(54) CYCLIC PEPTIDES, METHOD FOR PREPARING AND USE AS ANGIOGENESIS INHIBITORS OR ACTIVATORS

(75) Inventors: Natacha Betz, Ville d'Avray (FR); Juliette Boulard, legal representative, Sevres (FR); Antonin Boulard, legal representative, Sevres (FR); Liliane Dequaire, legal representative, Puteaux (FR); Romane Boulard, legal representative, Puteaux (FR); Sara Boulard, legal representative, Puteaux (FR); Andreas Bikfalvi, Gradignan (FR); Gerard Deleris, Bordeaux (FR); Julie Deleris, legal representative, Bordeaux (FR); Christiane Deleris, legal representative, Bordeaux (FR); Marie Deleris, legal representative, La Reunion (FR)

(73) Assignees: Commissariat a l'Energie Atomique, Paris (FR); Universite Victor Sagalen Bordeaux 2, Bordeaus Cedex (FR); Universite de Bordeaux 1, Talence Cedex (FR)

(21) Appl. No.: 12/418,101

(22) Filed: Apr. 3, 2009

Related U.S. Patent Documents

Reissue of:

(64) Patent No.: 7,199,100
Issued: Apr. 3, 2007
Appl. No.: 10/381,734
PCT Filed: Oct. 2, 2001
PCT No.: PCT/FR01/03049
§ 371 (c)(1),
(2), (4) Date: Apr. 3, 2003
PCT Pub. No.: WO02/28895
PCT Pub. Date: Apr. 11, 2002

(30) Foreign Application Priority Data

Oct. 4, 2000 (FR) ..... 00 12654

(51) Int. Cl.
*A61K 38/12* (2006.01)
*A61K 38/10* (2006.01)
*A61K 38/08* (2006.01)

(52) U.S. Cl. ..... 514/21.1; 514/21.4; 514/21.5; 514/21.6; 514/21.7; 530/317; 530/326; 530/327; 530/328; 530/329

(58) Field of Classification Search ..... None
See application file for complete search history.

(56) References Cited

U.S. PATENT DOCUMENTS 5,849,692 A 12/1998 Jonczyk et al.
5,939,383 A * 8/1999 Remacle et al. ..... 514/9

FOREIGN PATENT DOCUMENTS

EP 0 844 252 5/1998
WO 99 40947 8/1999
WO 00 53219 9/2000

OTHER PUBLICATIONS

B. Ivanov et al.: "Synthesis and use of a new bromoacetyl-derivatized heterotrifunctional amino acid for conjugation of cyclic RGD-containing peptides derived from human bone sialoprotein" Bioconjugate Chemistry, vol. 6, pp. 269-277, 1995.
D. Delforge et al.: "Solid-phase synthesis of tailed cyclic peptides: the use of alpha-allyl-protected aspartic acid leads to aspartimide and tetramethylguanidium formation" Letter In Peptide Science, vol. 3, pp. 89-97, May 1, 1996.
S.A. Kates et al.: "Automated allyl cleavage for continuous-flow synthesis of cyclic and branched peptides" Analytical Biochemistry, vol. 212, pp. 303-310 1993.
LG Presta et al.: "Humanization of an anti-vascular endothelial growth factor monoclonal antibody for the therapy of solid tumors and other disorders" Cancer Res., vol. 57, No. 20, pp. 4593-4599, Oct. 1997.
N. Ortega et al.: "Systemic activation of the vascular endothelial growth factor receptor KDR/flk-1 selectivity triggers endothelial cells with an angiogenic phenotype" Am J Panthol. vol. 151, No. 5, pp. 1215-1224, Nov. 1997.
Yves A. Muller et al.: "The crystal structure of vascular endothelial growth factor (VEGF) refined to 1.93 A resolution: multiple copy flexibility and receptor binding" Structure, vol. 5, No. 10, pp. 1325-1338, Oct. 15, 1997.
Svitlana Chetyrkina et al.: "Synthesis of N-Fmoc-4-[(diethylphosphone)-2', 2'-difluoro-1'-hydroxyethyl]phenylalanine, a novel phosphotyrosyl mimic for the preparation of signal transduction inhibitory peptides" Tetrahedron Letters vol. 41, pp. 1923-1926, 2000.
Roselyne Binetruy-Tournaire et al.: "Identification of a peptide blocking vascular endothelial growth factor (VEGF)-mediated angiogenesis" The EMBO Journal, vol. 19, No. 7, pp. 1525-1533, 2000.
Martin Hagedorn et al.: "Target molecules for anti-angiogenic therapy: from basic research to clinical trials" Critical Reviews in Oncology/Hematology, vol. 34, pp. 89-110, 2000.
Christine Piossek et al.: "Vascular endothelial growth factor (VEGF) receptor II-derived peptides inhibit VEGF" The Journal of Biological Chemistry, vol. 274, No. 9, pp. 5612-5619 1999.
Frederic Jonca et al.: "Cell release of bioactive fibroblast growth factor 2 by exon 6-encoded sequence of vascular endothelial growth factor" The Journal of Biological Chemistry, vol. 272, No. 39, pp. 24203-24209, 1997.
Napoleone Ferrara et al.: "Clinical applications of angiogenic growth factors and their inhibitors" Nature Medicine, vol. 5, No. 12, pp. 1359-1364, Dec. 1999.

(Continued)

*Primary Examiner* — Satyanarayana R Gudibande
(74) *Attorney, Agent, or Firm* — Oblon, Spivak, McClelland, Maier & Neustadt, L.L.P.

(57) ABSTRACT

The invention relates to cyclopeptides, the method of their preparation and their utilization as inhibitors or activators of angiogenesis.
These cyclopeptides [comprise] *contain* the following peptide sequence:

-Arg-Ile-Lys-Pro-His-Gln-Gly- (*SEQ ID NO: 1*).

They can be used in systems for inhibition of angiogenesis that [comprises] *include* a support [(1)], to which the cyclopeptide is [affixed by means of] *coupled via* an organic spacer arm [(3)] that may be provided with a moiety [(4)] capable of being [spliced] *cleaved* by an enzyme system.

126 Claims, 3 Drawing Sheets

OTHER PUBLICATIONS

D. Scott Wilbur et al.: "Biotin reagents for antibody pretargeting, 3. Synthesis, radioiodination, and evaluation of biotinylated starburst dendrimers" Bioconjugate Chem., vol. 9, pp. 813-825, 1998.

Katherine D. McReynolds et al.: "Syntehsis of biotinylated glycoconjugates and their use in a novel ELISA for direct comparison of HIV-1 Gp120 recognition of GalCer and related carbohydrate analogues" Bioconjugate Chem., vol. 10, pp. 1021-1031, 1999.

Yasufumi Sato et al.: "Autocrine activities of basic fibroblast growth factor: regulation of endothelial cell movement plasminogen activator synthesis, and DNA synthesis" The Journal of Cell Biology, vol. 107, pp. 1199-1205, Sep. 1988.

Oliver Seltz et al.: "HYCRON, an allylic anchor for high-efficiency solid phase synthesis of protected peptides and glycopeptides" J. Org. Chem., vol. 62, pp. 813-826, 1997.

Wayne J. Fairbrother et al.: "Novel peptides selected to bind vascular endothelial growth factor target the receptor-binding site" Biochemistry, vol. 37, pp. 17754-17764, 1998.

Bertrand Carboni et al.: "Aliphatic amino azides as key building blocks for efficient polyamine syntheses" J. Org. Chem., vol. 58, pp. 3736-3741 1993.

Haimanot Bekele et al.: "Improved synthesis of the Boc and Fmoc derivatives of 4-(4'-aminoethyl)-6-dibenzofuranpropionic acid: an unnatural amino acid that nucleates beta-sheet folding" J. Org. Chem., vol. 62, pp. 2259-2262, 1997.

* cited by examiner

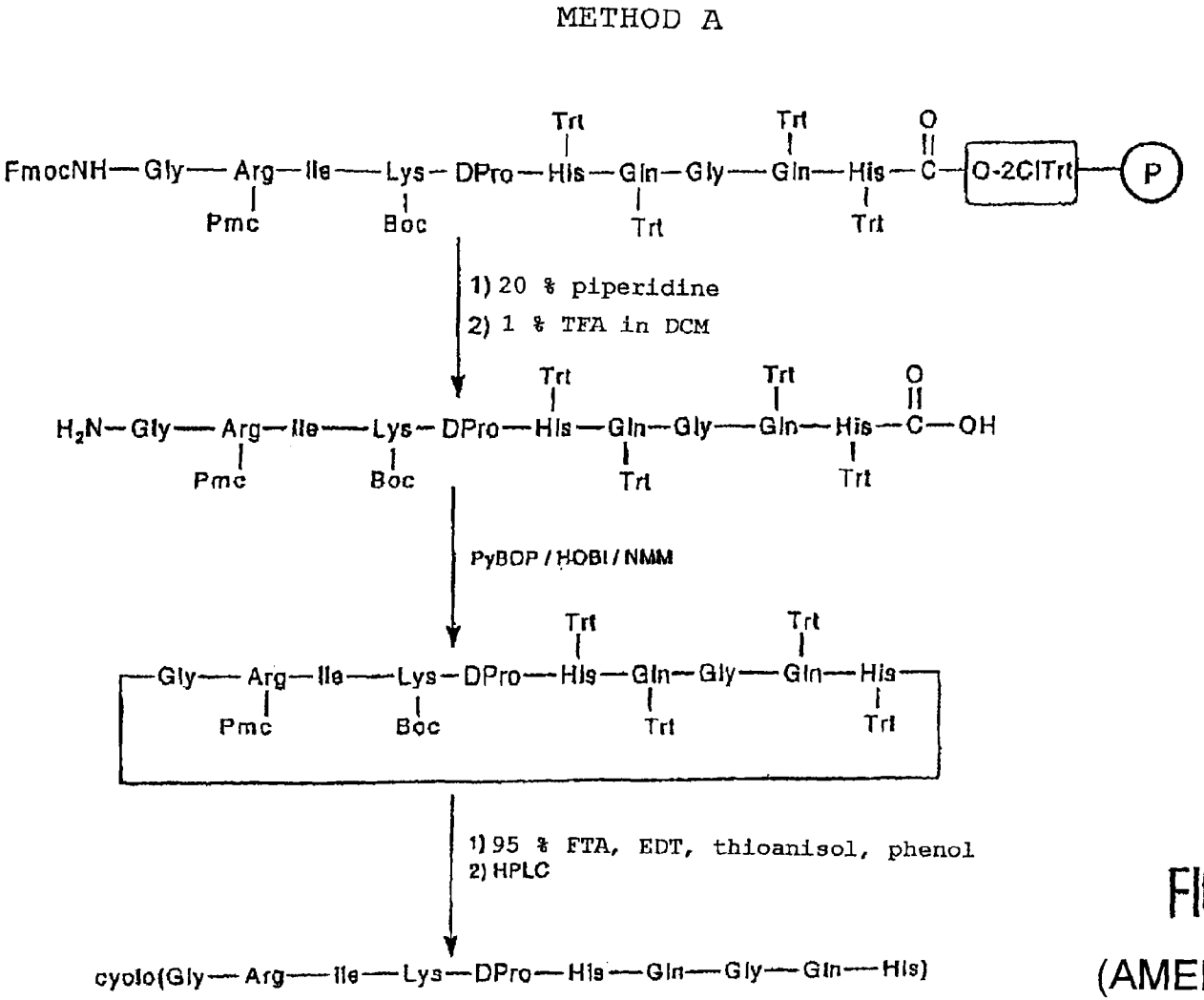
FIG. 1
(AMENDED)

FIG. 2
(AMENDED)
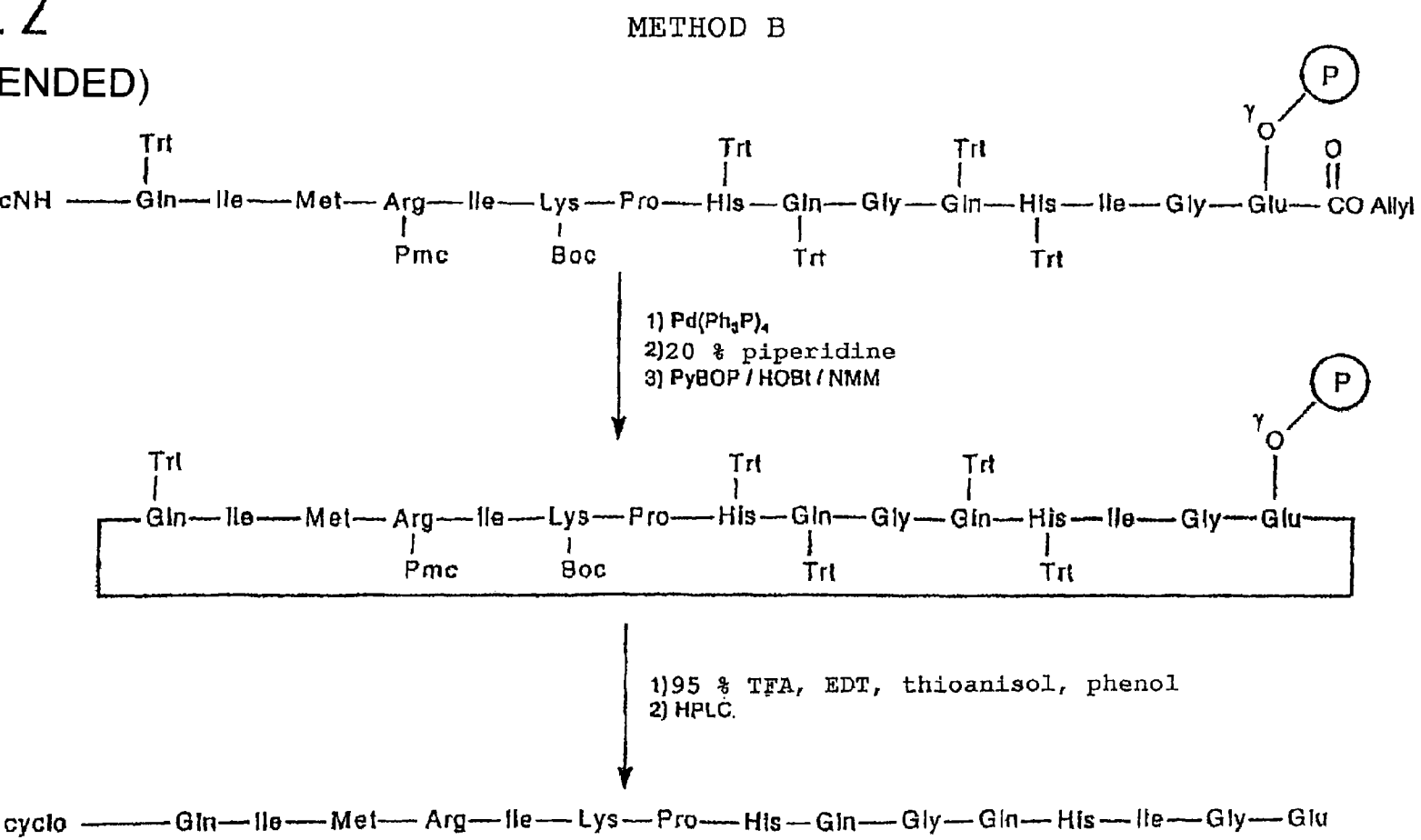

CYCLIC PEPTIDES, METHOD FOR PREPARING AND USE AS ANGIOGENESIS INHIBITORS OR ACTIVATORS

Matter enclosed in heavy brackets [ ] appears in the original patent but forms no part of this reissue specification; matter printed in italics indicates the additions made by reissue.

TECHNICAL FIELD

The object of the present invention is novel cyclopeptides and systems comprising them that enable control of angiogenesis.

Angiogenesis is a mechanism of neovascularization originating from a pre-existing capillary network. It is particularly important and indispensable in the course of many physiological processes such as embryonic development, implantation of the placenta, but also in different pathologies, in particular in tumor growth, development of metastases, ischemia, vascular diseases of the eye and chronic inflammatory diseases (see Ferrara et al, Nature Medicine, Vol. 5, N° 12, December 1999, pp. 1361-1364 [1] and Hagedorn and Bikfalvi [2]). Angiogenesis is also essential in tissue regeneration and permanent colonization of the biomaterial implants such as bone replacements.

Angiogenesis is a multistage process that initially invokes migration, the attachment and adhesion of the endothelial cells and then their proliferation and organization into tubes, in order to form the vascular network necessary to the development of the tissues.

Among the factors regulating angiogenesis, vascular endothelial growth factor (VEGF) appears to be the most important ones.

VEGF exists in four isoforms: A, B, C and D and of these, isoform A, which comprises 165 amino acids, is a powerful regulator of tumor angiogenesis and appears to be involved in other pathologies such as diabetic retinopathy or chronic inflammatory diseases.

VEGF-A is produced by normal or transformed cells. Its expression can be induced by hypoxia, oncogene activation or activation by growth factors such as fibroblast growth factor PGF-2.

VEGF-A binds to different receptors, especially the kinase domain receptor KDR (VEGFR-2), which appears to be a very important effector in pathological angiogenesis. Also, inhibition of angiogenesis through the KDR receptor could constitute an interesting therapeutic approach.

The structure of VEGF-A which comprises 165 amino acids, was described at the end of 1997 and was accessible at the end of June 1998, as disclosed in the document (see Muller Y. A. in Structure, 1997, 5, pp. 1325-1338 [3]).

BACKGROUND ART

A certain number of strategies have been developed for the purpose of interfering with the function of the KDR receptor of VEGF. They include inhibition of VEGF

- by humanized antibodies such as is described by Presta et al in Cancer Research, 57 1997, pp. 4593-4599 [4];
- by anti-idiotype antibodies as is described by Ortéga et al in Am. J. Pathol., November 1997, 151(5), pp. 1215-1224 [5];
- by inhibitors of the tyrosine kinase domain of the KDR receptor as is described by Piossek et al in The Journal of Biological Chemistry, Vol. 274, [N°] *No.* 9, 1999, pp. 5612-5619 [6], and

- by peptide inhibitors isolated by phage display as is described by Fairbrother et al in [Biochemisry] *Biochemistry* 37, 1998, pp. 17754-17764 [7].

Other molecules active relative to angiogenesis have been characterized and certain ones have entered into the clinical phase in oncology as is described by Hagedorn and Bikfalvi in Critical Reviews in Oncology/Hematology, 34, 2000, pp. 89-110 [2].

The U.S. Pat. No. 5,939,383 [8] patent teaches the utilization of diverse cyclopeptides tailed or coupled to a solid or other support for applications in biotechnology. Of the various possibilities, he proposes the following cyclopeptide:

cyclo(Glu-Gln-Ile-Met-Arg-Ile-Lys-Pro-His-Gln) (SEQ ID NO:24)

for the KDR receptor of VEGF.

However, it does not provide any results on the possible inhibition of the KDR receptor by this [cyclo peptide] *cyclopeptide* and, as will be seen in the following, it does not result in the inhibition of binding of VEGF to its receptor.

SUMMARY OF THE INVENTION

The object of the present invention is specifically novel cyclopeptides having an affinity for binding with the KDR receptor that is higher than that provided by the products mentioned above, which makes possible their utilization in systems activating or inhibiting angiogenesis.

A further object of the invention is a cyclopeptide comprising the peptide sequence:

-Arg-Ile-Lys-Pro-His-Gln-Gly- (SEQ ID NO: 1)

In this peptide sequence, the presence of three amino acids Arg, Lys and His is essential for obtaining a desired interaction with the KDR receptor of the VEGF.

In the invention, the Arg and Gly residues of the cyclopeptide are connected by a chain that can comprise one or a plurality of organic molecules chosen from the group comprising the natural and synthetic amino acids, or compounds comprising a COOH group and an $NH_2$ group possibly substituted. The amino acids can be in the L form or in the D form.

The synthetic amino acids can be, for example, aromatic and/or heterocyclic compounds comprising a COOH group and an $NH_2$ group on a structure allowing a spatial conformation close to that of VEGF at the peptide sequence of interest [(SEQ I.D. N°: 1)] (*SEQ ID NO: 1*).

The aromatic parts can be derivates of benzene, naphthalene, dibenzofurane.

The heteroatoms can be atoms of oxygen, nitrogen, silicon, germanium, tin or phosphorous.

By way of example of an amino acid of this type, [4-(2'amino ethyl)-6-dibenzo furan propanoic acid] *4-(2'amino ethyl)-6-dibenzofuran propanoic acid* can be cited having the formula:

(I)

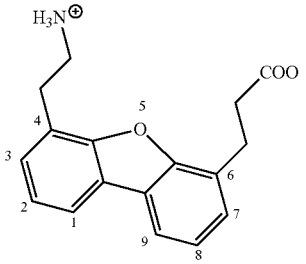

Synthesis of this acid has been described by Bekele et al, J. Org. Chem. 63, 1997, pp. 2259-2262 [9].

By way of example of organic compounds that can be utilized, one can cite the silaxanthenes, [4-(2'-amino ethyl)-6-(dibenzo furan) propanoic acid] *4-(2'-amino ethyl)-6-(dibenzofuran) propanoic acid* and 5-(2'-amino ethyl)-9,9-dimethyl-sila-xanthene-4-propanoic acid.

When the compound comprises a substituted $NH_2$ group it can be of the NHR type wherein R is a hydrocarbon group eventually comprising functional groups of the carboxy, ester, ether, hydroxy and siloxy type.

Preferably, the chain that links the ends of the peptide sequence [(SEQ I.D. N°: 1)] (*SEQ ID NO: 1*) described above comprises an amino acid in the D configuration, preferably. D-Phe or D-Tyr.

By way of example of cyclopeptides conforming to the invention, the following peptides can be cited:

| | | |
|---|---|---|
| P7: | cyclo(Gly-Arg-Ile-Lys-DPro-His-Gln-Gly-Gln-His) | SEQ ID NO: 2 |
| P8: | cyclo(Gly-Arg-Ile-Lys-Pro-His-Gln-Gly-His) | SEQ ID NO: 3 |
| P9: | cyclo(Pro-Arg-Ile-Lys-Pro-His-Gln-Gly-Gln-His) | SEQ ID NO: 4 |
| P11: | cyclo(DPhe-Pro-Gln-Ile-Met-Arg-Ile-Lys-Pro-His-Gln-Gly-Gln-His-Ile-Gly-Glu) | SEQ ID NO: 5 |
| P12: | cyclo(Gly-Gln-Ile-Met-Arg-Ile-Lys-Pro-His-Gln-Gly-Gln-His-Ile-Gly-Glu) | SEQ ID NO: 6 |
| P13: | cyclo(Pro-Gln-Ile-Met-Arg-Ile-Lys-Pro-His-Gln-Gly-Gln-His-Ile-Gly-Glu) | SEQ ID NO: 7 |
| P16: | cyclo(Arg-Ile-Lys-Pro-His-Gln-Gly) | SEQ ID NO: 8 |
| P17: | cyclo(Pro-Arg-Ile-Lys-Pro-His-Gln-Gly) | SEQ ID NO: 9 |
| P19: | cyclo(Gln-Ile-Met-Arg-Ile-Lys-Pro-His-Gln-Gly-Gln-His-Ile-Gly-Glu) | SEQ ID NO: 10 |
| P20: | cyclo(DPhe-Pro-Gln-Ile-Met-Arg-Ile-Lys-Pro-His-Gln-Gly-Gln-His-Ile-Gly) | SEQ ID NO: 11 |
| P21: | cyclo(DPhe-Pro-Ile-Met-Arg-Ile-Lys-Pro-His-Gln-Gly-Gln-His-Ile) | SEQ ID NO: 12 |
| P23: | [cyclo(DPhe-Pro-Arg-Ile-Lys-Pro-][His-Gln)] *cyclo(DTyr-Pro-Arg-Ile-Lys-Pro-His-Gln)* | SEQ ID NO: 13 |
| P24: | cyclo(Gly-Arg-Ile-Lys-Pro-His) | SEQ ID NO: 25 |

The cyclopeptides of the invention can be used for controlling angiogenesis and treating the diverse pathologies associated with angiogenesis. They can be utilized for these applications in the form of solution or in systems or biomaterials.

In the case, wherein the cyclopeptides are utilized in the form of a solution, it is generally an aqueous solution that can be administered by oral route or is injectable. The cyclopeptide can be utilized either to assure inhibition of angiogenesis by binding of the cyclopeptide on a VEGF receptor, or for assuring activation of angiogenesis by coupling two cyclopeptides on an organic compound suitable for conferring upon them an efficacious spatial configuration, allowing dimerization of the VEGF receptors.

In both cases the cyclopeptides may be attached if necessary to bioactive agents.

Also, a further object of the invention is a composition comprising a cyclopeptide chosen from the following cyclopeptides:

| | | |
|---|---|---|
| P11: | cyclo(DPhe-Pro-Gln-Ile-Met-Arg-Ile-Lys-Pro-His-Gln-Gly-Gln-His-Ile-Gly-Glu) | SEQ ID NO: 5 |
| P16: | cyclo(Arg-Ile-Lys-Pro-His-Gln-Gly) | SEQ ID NO: 8 |
| P17: | cyclo(Pro-Arg-Ile-Lys-Pro-His-Gln-Gly) | SEQ ID NO: 9 |
| P19: | cyclo(Gln-Ile-Met-Arg-Ile-Lys-Pro-His-Gln-Gly-Gln-His-Ile-Gly-Glu) | SEQ ID NO: 10 |
| P20: | cyclo(DPhe-Pro-Gln-Ile-Met-Arg-Ile-Lys-Pro-His-Gln-Gly-Gln-His-Ile-Gly) | SEQ ID NO: 11 |
| P23: | [cyclo(DPhe-Pro-Arg-Ile-Lys-Pro-][His-Gln)] *cyclo(DTyr-Pro-Arg-Ile-Lys-Pro-His-Gln)* | SEQ ID NO: 13 |
| P24: | cyclo(Gly-Arg-Ile-Lys-Pro-His) | SEQ ID NO: 25 |

Further still, an object of the invention is a pharmaceutical preparation for activating angiogenesis comprising two identical or different cyclopeptides coupled with a pharmaceutically acceptable organic compound, the cyclopeptides being chosen from the following cyclopeptides:

| | | |
|---|---|---|
| P11: | cyclo(DPhe-Pro-Gln-Ile-Met-Arg-Ile-Lys-Pro-His-Gln-Gly-Gln-His-Ile-Gly-Glu) | SEQ ID NO: 5 |
| P16: | cyclo(Arg-Ile-Lys-Pro-His-Gln-Gly) | SEQ ID NO: 8 |
| P17: | cyclo(Pro-Arg-Ile-Lys-Pro-His-Gln-Gly) | SEQ ID NO: 9 |
| P19: | cyclo(Gln-Ile-Met-Arg-Ile-Lys-Pro-His-Gln-Gly-Gln-His-Ile-Gly-Glu) | SEQ ID NO: 10 |
| P20: | cyclo(DPhe-Pro-Gln-Ile-Met-Arg-Ile-Lys-Pro-His-Gln-Gly-Gln-His-Ile-Gly) | SEQ ID NO: 11 |
| P23: | [cyclo(DPhe-Pro-Arg-Ile-Lys-Pro-][His-Gln)] *cyclo(DTyr-Pro-Arg-Ile-Lys-Pro-His-Gln)* | SEQ ID NO: 13 |
| P24: | cyclo(Gly-Arg-Ile-Lys-Pro-His) | SEQ ID NO: 25 |

The pharmaceutically acceptable organic compound can comprise alternated hydrophilic-hydrophobic sequences and reactive functions with the functions of side chains of amino acids of the cyclopeptide.

When the cyclopeptides are used in the form of systems or biomaterials, the latter also capable of being produced so as to assure either inhibition or activation of angiogenesis.

According to a first embodiment of these systems, they comprise one or a plurality of cyclopeptides, each bonded covalently to one organic spacer arm that can itself be covalently bonded to a support.

With the first embodiment, when the system is in contact with the VEGF receptors, one sole cyclopeptide affixes to a VEGF receptor and prevents dimerization of the receptor and activation of angiogenesis.

According to a second embodiment of these systems, more particularly for assuring activation of angiogenesis, they can comprise two cyclopeptides bonded covalently to an organic compound in order to dispose the two cyclopeptides in a efficacious spatial configuration for activating angiogenesis.

The organic compounds are pharmaceutically acceptable compounds. [The] *They* can be formed of alternated hydrophilic-hydrophobic sequences, for example, of the [glycol/alkane polyethylene] *polyethylene glycol/alkane* or fluoro alkane type and comprise functions reactive with the amine, hydroxy, carboxylic acid or other functions of the side chains of the cyclopeptide in order to assure its fixation on the compound; they can also comprise acrylic functions.

By way of example of a compound of this type, one can cite the compound having the formula:

$$HOOCH_2CH_2(CH_2CH_2O)_5(CH_2)_3—NH—(CH_2CH_2O)_5CH_2—CH_2—COOH$$

which comprises two carboxylic functions capable of reacting with the hydroxy or amino functions of the side changes of the amino acids of the cyclopeptide.

The organic compounds that can be used can also comprise aromatic parts and/or heteroatoms so as to maintain, on the one hand, the two cyclopeptides in an efficacious configuration and to allow, on the other hand, fixation of the two cyclopeptides in this configuration on different supports.

The aromatic parts can be derivates of benzene, naphthalene, dibenzofurane.

The heteroatoms can be oxygen. nitrogen, silicon, germanium, tin or phosphorous atoms.

[in] *In* order to assure activation of angiogenesis, the distance between the two cyclopeptides fixed on the organic compound is such that, when the system is put in contact with the cells expressing the receptors of the vascular endothelium growth factor VEGF, it allows dimerization of said receptors.

In this second embodiment, the organic compound supporting the two cyclopeptides is generally connected to a support by means of an organic spacer arm.

In these two embodiments of the systems according to the invention, the spacer arm comprises, for example, a hydrocarbon, fluorocarbon, polyether, polyethylene glycol. polyamine, polyamide, polyester, polysiloxane chain or a combination of these, which is functionalized at each end in order to form a covalent bond, on the one hand, with the cyclopeptide and, on the other hand, with the support.

Preferably the organic spacer arm further comprises a moiety or a peptide sequence capable of being cut by an enzyme system.

Cutting of the spacer arm thus makes possible release of the active cyclopeptides at the targeted locations. The enzyme system can be comprised of metalloproteases of the extracellular matrix or other enzymes.

In this instance, the moiety is a peptide sequence that is a substrate of said metalloproteases of the extracellular matrix such as the following peptide sequence, for example:

HOOC-Ala-Gly-Leu-Leu-Gly-Gln-Pro-Gly-$NH_2$ (*SEQ ID NO: 26*).

According to an advantageous disposition of the invention, the spacer arm can comprise in addition bioactive compounds that will also be released to the desired location at the time of cutting the spacer arm.

Said bioactive compounds can be cytotoxic agents, anticancer agents or any other active principle, for example, that one would want to use at the level of the KDR receptors.

According to the invention, the support on which the cyclopeptide(s) can be affixed can be an organic or inorganic solid. In particular, an organic polymer in solid form or in gel form could be used as the support.

The polymer utilized is advantageously a biocompatible polymer, biodegradable or nonbiodegradable.

By way of example of polymers that can be used, one can cite ethylene polyterephthalate, the copolymers of vinylidene fluoride and hexafluoropropylene, the polyvinyl alcohols, polyhydroxy ethyl methacrylate, polysaccharides and the copolymers obtained from monomers entering into the constitution of the aforesaid polymers.

The cyclopeptides of the invention can be prepared by methods implementing an automatic synthesis step of a linear peptide on a solid phase by a conventional process, followed by coupling of the ends of the linear peptide either after having released the peptide from the solid phase or by then releasing it from the solid phase.

Thus, according to a first embodiment, the process comprises:

a) preparing a linear peptide by chemical synthesis on a solid phase;

b) releasing the linear peptide from the solid phase, and c) coupling the ends of the linear peptide to form the cyclopeptide.

According to a second embodiment, the process comprises:

a) preparing a linear peptide by chemical synthesis on a solid phase;

b) coupling the free end of the linear peptide with a terminal function of an amino acid residue of the linear peptide, and c) releasing the cyclopeptide from the solid phase.

Further still, an object of the invention is a method for preparing a system comprising a support on which the cyclopeptide(s) is (are) affixed, which comprises subjecting an organic polymer support to irradiation by ionizing, plasma or photon beams on defined zones of the support and to then grafting onto said zones of the support an organic spacer arm on which the cyclopeptide will be attached.

Generally, the radiation is done using a mask in order to define the zones to be modified on the support. The ionizing radiation used can be electron beams or accelerated heavy ion beams.

In this process, the cyclopeptides can be affixed on the organic spacer arms prior to grafting. Their fixation can also be realized after grafting and in this instance, the process further includes a step for fixation of the cyclopeptides on the organic spacer arm after grafting of same.

Other features and advantages of the invention will become more apparent when reading the following description exemplary embodiments given are understood to be illustrative and non-limiting—with reference to the attached figures.

BRIEF DESCRIPTION OF THE DRAWINGS

FIG. 1 represents the first embodiment of synthesis of a cyclopeptide according to the invention (schematic representation using the [sequence of SEQ ID NO: 2] *sequences of SEQ ID NOS: 29, 29, 2 and 2, respectively, in order of appearance*);

FIG. 2 represents the second embodiment of synthesis of a cyclopeptide according to the invention (schematic representation using the [sequence of SEQ ID NO: 10] *sequences of SEQ ID NOS: 30, 10 and 10, respectively, in order of appearance*);

DETAILED SPECIFICATION OF THE EMBODIMENTS OF THE INVENTION

Figure 3:
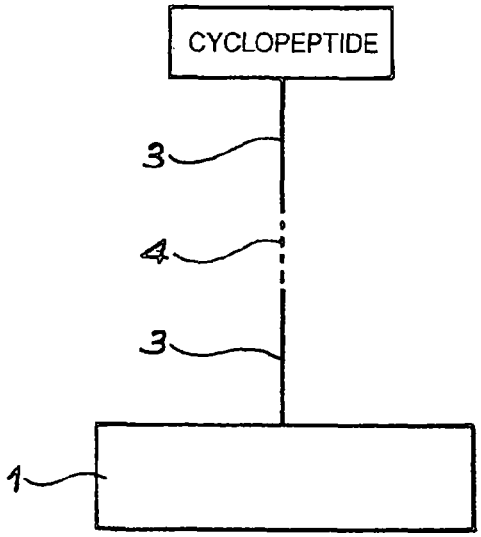
FIG. 3 represents binding of a cyclopeptide according to the invention onto a support by means of an organic spacer arm.

In the following the chemical synthesis of the peptides P1 to P22 is described in Table 1, which comprise the sequences corresponding to the segments β5-β6 of the vascular endothelium growth factor (VEGF-A).

The peptides P1 to P6, P10, P14, and P15 are linear peptides and peptides P7 to P9, P11, P12, P13 and P16 to P24 are cyclopeptides.

Cyclopeptides P7 to P9, P11, P12, P13, P16 to P18 and P23 are prepared using synthesis method A; that is, the first embodiment of the process for synthesizing the cyclopeptides of the invention.

Cyclopeptides P12, P13 and P19 to P22 are prepared using the synthesis method B; that is, the second embodiment of the process for synthesizing the cyclopeptides of the invention.

In the description of these syntheses that follows, the following abbreviations have been used:

Fmoc: 9-fluoroenyl methoxy carbonyl
tBu: t-butoxycarbonyl
Trt: trityl
2-Cl Trt: 2-chlorotrityl
HMPB: 4-hydroxy methyl-3-methoxy phenoxy butyric acid
BHA: benzhydryl amine
HOBt: N-hydroxy benzotriazole
DCC: N,N'-dicyclohexyl carbodiimide
DCM: dichloromethane
TFA: trifluoroacetic acid
DIEA: N,N-diisopropyl ethylamine
NMM: N-methyl morpholine
PyboP: Triazole-1-yl-oxy-tris-pyrrolidino-phosphonium hexafluoro phosphate
NMP: N-methylpyrrolidone
DIPCDI: N,N-diisopropyl carboiimide
DMAP: 4-dimethyl amino pyridine
FCS: Fetal calf serum
PBS: Phosphate buffered saline solution
DMEM: Delbecco modified minimal essential medium
HEPES: N-(2-Hydroxyethyl)piperazine-N'-2-ethane sulfonic acid Synthesis method A is represented in FIG. 1 which shows the synthesis of cyclopeptide P7.

According to this method, at the very beginning the linear peptide is synthesized on a solid phase P by batch synthesis using the Fmoc/tBu protection technique and an Applied Biosystems 430A automatic synthesizer. For the preparation of the protected peptide fragments, pre-charged acid-labile 2-chlorotrityl resins are used, for example the H-His(Trt)-2-ClTrt and H-Ile-2-ClTrt resins or HMPB-BHA resins on a base of BHA polystyrene functionalized using a linker that is Rinker's 4-hydroxymethyl-3-methoxy-phenoxybutanoic acid, for example Fmoc-Gly-HMPB-BHA.

The amino acids protected by the 9-fluorenyl methoxy carbonyl [(Pmoc)] (*Fmoc*) group are [couple] *coupled* using an excess corresponding to four-times the quantity of amino acid activated relative to N-hydroxybenzotriazole (HOBt) ester by means of N,N'-dicyclohexyl [cardodiimide] *carbodiimide* (DCC).

In FIG. 1, the first line represents the linear peptide, whose side chains re protected either by the trityl groups (Trt) in the case of the amino groups of His and [Gly] *Gln*, the Boc (t-butyloxy carbonyl) group in the case of the *amino group of Lys and the* 2,2,5,7,8-pentamethyl-chromane-6-sulfonyl (Pmc) in the case of Arg.

One then proceeds to the separation of the linear peptide of the solid phase P by treatment with a 1% trifluoroacetic acid (TFA) solution in dichloromethane (DCM).

Thus, a protected peptide fragment is obtained with a high yield and high degree of purity and negligible loss of the groups protecting the side chains of the amino acids.

Repeat treatment of the peptidyl resin with a fresh solution of TFA and minimal reaction times (ten times over the period of 2 minutes) give the best results. The resin is then washed several times with DCM and methanol. Cutting is followed by thin layer chromatography. The combined filtrates are evaporated under reduced pressure and iced water is added to the residue in order to precipitate the peptide material. The raw material is isolated by filtration, washed with fresh water and dried in a desiccator under high vacuum over NaOH. The protected linear peptides are analyzed by reverse phase high performance liquid chromatography HPLC (Merck RP-18 LiChrosorb column, 7 μm, 0.4×25 cm) using a linear gradient going from 70 to 100% of B into A, solvent A being an aqueous solution of 0.1% TFA and solvent B being an aqueous solution of [FFA] *TFA* 0.1% and 70% acetonitrile.

The protected linear peptide corresponding to P7 is shown in FIG. 1.

One then proceeds to cyclization of the protected linear peptide. For this purpose, it is dissolved in some DCM in order to obtain a final concentration of 1 mg/ml. 6 equivalents of N,N-diisopropyl ethylamine (DIEA) or N-methyl-morpholine (NMM) is added to the solution and cyclization is carried out by means of benzotriazole-1-yl-oxy-tris-pyrrolidino-phosphonium hexafluoro phosphate (PyBOP)/N-hydroxybenzotriazole (HOBt) by using three equivalents of each coupling reagent. The reaction milieu is maintained at 25° C. under nitrogen atmosphere and gentle stirring for 24 to 48 hours until cyclization is complete, which is verified by HPLC.

The solvent is eliminated by evaporation under reduced pressure and iced water is added to the residue. The crude precipitate is removed by filtration, washed in fresh water, dried in a desiccator under high vacuum over NaOH and it is used for total deprotection of the side chains without complementary purification.

The protected cyclopeptide corresponding to P7 is shown in FIG. 1.

Deprotection side chains of the cyclopeptide is done by means of a 95% TEA solution in the presence of reagents (phenol, thioanisol, triisopropyl silane, water) over 2 to 3 hours. One then evaporates the greater part of the TFA in order to obtain a satisfactory precipitation of the deprotected crude cyclopeptide and 10-times the volume of ice-cooled ether is added. After filtration and washing with fresh ether, the precipitate is dried over NaOH and lyophilized. Then semi-preparative purifications are effected over an Applied Biosystems HPLC column using the LiChrosorb C18 reverse phase column (250×10). Buffers A and B described above are used. Linear gradients of 10 to 50% of B in A over a period of 30 minutes at a flow of 4 ml/min are used. The homogeneous fractions obtained by HPLC are combined and they are lyophilized in order to obtain the desired cyclopeptides with a satisfactory purity of greater than 95% by analytical HPLC.

FIG. 1 shows the protected cyclopeptide, then the deprotection step culminating in the cyclopeptide P7 of Table 1.

The same operational procedure is followed in order to prepare peptides P8, P9, P11, P12, P13, P16 to P18 and P23 by using for the synthesis of the L or D amino acids protected by the Fmoc group, Fmoc-L-Gly-HMPB/BHA (0.53 mmol/g) resin, H-His(Trt)-2-ClTrt (0.42 mmol/g) resin, H-Ile-2-ClTrt (0.53 mmol/g) resin, and NovaSyn TGA (90 μm) resin, and PyBOP obtained from Novabiochem.

The HOBt, DCC, TFA, DIEA, NMM and piperidine reagents obtained from Aldrich were also used.

The HPLC was done on Merck LiChrosorb RP-18 (7 μm, 0.4×25 cm) columns and on Interchim LiChrosorb C-18 (5 μm, 0.4×25 cm) columns by performing elution with a linear gradient of solvent B in solvent A. Solvent A comprises 0.1% TFA in $H_2O$. Solvent B comprises 0.1% TFA, 70% [acetonitryl] *acetonitrile* and 30% water. A flow of 1 ml/min over a period of 30 minutes was used. UV detection was done at 214 nanometers and 280 nanometers. The purified peptides are characterized by amino acid analysis by performing hydrolysis in HCl 6 M and 2% phenol at 110° C. for 20 to 24 hours and by FAB-MS mass spectrometry.

Synthesis method B or the second embodiment of the process for synthesizing cyclopeptides according to the invention will now be described.

Synthesis method B is shown in FIG. 2 in the case of peptide P19.

The same reagents are used for this synthesis as were used for synthesis A by adding to it the Fmoc-L-Glu (PEG-PS)-OAllyl resin (0.18 mmol/g) from Perkin Elmer.

At the start, the P10 linear peptide is synthesized by synthesis on solid phase using the Applied Biosystems 430 A automatic synthesizer, as described in synthesis method A.

As shown in FIG. 2, the first C-terminal amino acid Fmoc-Glu-OAllyl is attached to the NovaSyn TGA 90 μm (solid phase P) resin by its side chain using a symmetrical anhydride method. The resin is expanded in the N-methylpyrrolidone (NMP) for 30 minutes. A solution of 5 equivalents of N,N-diisopropyl carbodiimide (DIPCDI) is added to a solution of 10 equivalents of amino acid in some dry DCM at 0° C. After stirring for 30 minutes, the solvent is removed under reduced pressure and the residue is dissolved in NMP and transferred to the pre-impregnated resin. Fixation of the carboxylic acid is done by esterification catalyzed by 4-dimethyl amino pyridine (DMAP) at a rate of 0.1 equivalent over 2 hours to give a final substitution of 0.25 mmol/g. The resin charge is estimated by UV quantification of the piperidine-Fmoc addition product at 290 nm. The commercial [Fmoc-L-Glu-(PEG-PS)-QAllyl] *Fmoc-L-Glu-(PEG-PS)-OAllyl* (0.18 mmol/g) resin obtained from Perkin Elmer was also used.

The resulting amino acids are coupled, protected by the Fmoc group by using an excess corresponding to 4 times the quantity of amino acid activated with respect to HOBt ester by means of DCC.

Thus, the linear peptide with protected side chains is obtained as represented in the first line of FIG. 2.

Allylic deprotection is then performed on the terminal Glu amino acid affixed to the solid phase by treating the resin with the protected peptide by 3 equivalents of $[Pd(PPh_3)_4]$ in a DCM:AcOH:NMM (37:2:1) under an argon current at 25° C. over a period of 2.5 hours while occasionally gently stirring. The catalyst is removed by washing the resin with 0.5% DIEA in NMP over a period of 2 minutes 3 times in NMP, then in sodium diethyldithiocarbamate 0.5% w/w in NMP and DCM over a period of 2 minutes and repeating 3 times.

Then cyclization of the peptide is done on the solid phase in the following manner. The resin is treated with 20% piperidine in NMP in order to release the N-terminal amino group from the peptide and it is then washed with HOBt 1 N in NMP, then with NMP and DCM. Cyclization is done in solid phase by using 6 equivalents of PyBOP, 6 equivalents of HOBt and 12 equivalents of DIEA in NMP over a period of 4 to 6 hours. Completion of cyclization is verified by the ninhydrine test. The resin is washed several times with MMP and DCM and then dried under high vacuum overnight. The protected cyclopeptide is represented in FIG. 2.

One then proceeds to the separation of the cyclopeptide from the solid phase and deprotection of the side chains of the amino acids. this is done by means of 95% TFA and the product of acidolysis is purified by semi-preparative HPLC as hereinbefore described.

The homogeneous fractions obtained by HPLC are combined by and lyophilized in order to obtain the desired cyclopeptides with a satisfactory degree of purity (greater than 95% by analytical HPLC).

In this manner, the P19 cyclopeptide as represented in FIG. 2 is obtained.

The same operational procedure is followed for preparing the P20 to P22 cyclopeptides shown in Table 1.

The linear peptides P1 to P6, P10, P14 and P15 of Table 1 are prepared by conventional peptide synthesis.

Table 2 shows the structure and the molecular mass of the P1 to P22 peptides by referencing the peptide sequence of VEGF-A which comprises 165 amino acids.

The P1 to P24 peptides are tested as concerns their property of inhibition of the binding of VEGF to its KDR receptor.

For these tests, heparin sulfate deficient Chinese hamster ovarian cells that are transfected with an expression vector containing VEGFR2cDnA (CHOm VEGFR2 cells) are used. It has been shown that the recombinant KDR of the CHO cells have the same characteristics as endothelial cell KDR (see Binétruy-Trournaire et al, EMBO Journal, 19, (7), 2000 pp. 1525-1533 [10]).

The CHOm VEGFR2 cells are obtained by transfection of the Chinese hamster ovarian cells that are deficient in heparin sulfate using VEGFR2 cDnA in a psV-7d vector as has been described by Jonca et al in J. Biol. Chem., 1997, 272, pp. 24203 [11]. The CHOm VEGFR2 cells are routinely cultured in Dulbecco modified Eagle medium and supplemented with 10% (v/v) fetal calf serum (FCS), 50 U/ml penicillin, 50 μg/ml streptomycin, 1 mg/ml glucose and 2 mM L-glutamine at 37° C. in a 5% $CO_2$ atmosphere.

For these tests, $^{125}$I-Na radiolabeled VEGF is used by utilizing iodine beads (Iodogen).

The $^{125}$I-VEGF specific activity is 150,000 to 200,000 cpm/ng. The cells are inoculated into 3.5 cm diameter flasks that have been previously coated with 0.15% gelatin using a density of 200,000 cells per flask and cultured in a complete medium over a period of 2 days. The subconfluent flasks are transferred at 4° C. The cells are washed twice in ice-cooled phosphate buffered saline (PBS) solution and incubated with different concentrations of peptides and 5 ng/mL of $^{125}$I-VEGF in the presence or absence of 50 ng/mL heparin in a binding buffer (DMEM containing 20 mmol/L HEPES, pH 7.4, 0.15% gelatin) over a period of 2 hours at 4° C. At the end of the incubation period, the cells are washed 3 times using iced PBS and solubized in 1 mL of buffer with 2% Triton X 100, 10% glycol, 1 mg/mL bovine serum albumin BSA. The radioactivity rate bound to the cells is counted in an MR-250 Kontron gamma counter. The non-specific binding is determined by incubation of the cells with $^{125}$I-VEGF and an 200-times excess of unlabeled VEGF. Specific binding is calculated by subtracting non-specific binding from total binding.

This assay is performed, preferably on fixed concentrations of the P1 to P22 peptides of 20 μM, 200 μM and 400 μM. All of the linear peptides and some cyclic peptides do not exhibit the inhibitor effect on binding of the VEGF to the KDR at these concentrations. These assays are continued using the cyclopeptides of interest and two linear peptides as controls for an inhibition analysis as a function of dose.

The results obtained represented by the $IC_{50}$ or the concentration in μM required to inhibit 50% of binding of VEGF to the KDR receptor are also given in Table 2.

All of the assays were repeated three times and give similar results.

It will thus be noted that the cyclopeptides P11, P16, P17, P19, P20, P23 and P24 are very effective in inhibiting binding of VEGF to the KDR receptor.

On the other hand, the P22 cyclopeptide that corresponds to the cyclopeptide described in U.S. Pat. No. 5,939,383 [8] is not more effective than the linear peptides P1 to P6, P10, P14 and P15 in inhibiting this binding.

The peptides inhibiting binding of the $^{125}$I-VEGF to the VEGFR2 receptor are then tested in in vitro, ex vivo and in vivo angiogenesis assays and relative to their effect on cellular signaling. The results concerning the effect of the active peptides on cellular proliferation, cellular migration and activation of the p42 and p44 kinases (MAP kinases; kinases activated by mitogens) are given here.

Cellular proliferation is measured by cell count. 7,000 endothelial cells are placed in the wells of 24-well plates (Costar) in DMEM medium containing newborn bovine serum. After the cells have adhered, the cells are washed in DMEM without serum and incubated with DMEM containing 1% newborn bovine serum, 10 ng/mL of VEGF in the presence or absence of different peptide concentrations. Two days later, the cells area once again stimulated by VEGF in the presence or absence of different concentrations of peptide. At the fifth day. the cells are trypsinized and counted using a Coulter counter. By way of example, the P11 (circular) peptide shows strong inhibition of cellular proliferation. On the other hand, the linear peptide is inactive (Table 3).

Cellular migration is measured according to the method described by Sato and Rifkin (J. Cell Biol., September, 1988, (107 (3): 1199-205) [17] with modifications. 100,000 endothelial cells are placed in 35 mm culture flasks in DMEM medium containing 10% fetal calf serum. On confluence, the medium is replaced by DMEM medium without serum and the cells are incubated overnight. On the next day, denudation is done artificially in the monolayer using a sterile pipette tip. A series of digital photographs is taken and the border of denudation is marked by a line using the BiocomVision-Lab2000 program. The flasks are then rinsed and incubated with 10 ng/mL VEGF in the presence or absence of peptide. After 18 hours of incubation a new series of photographs is taken and the before and after stimulation images are superimposed. The cells situated beyond the border of denudation are counted. For example, the P11 (cyclic) peptide in this type of assay strongly inhibits cellular migration. On the other hand, the linear peptide has no effect (Table 3).

Phosphorylation of ERK1 (p44) and ERK2 (p42) is measured by Western blot using anti p42/p44 antibodies (New England Biolabs). The capillary endothelial cells are cultivated in DMEM containing 10% newborn bovine serum. Subconfluent cultures are then deprived of serum over a period of 24 hours. The peptides are then added at specific concentrations over 5 minutes to the cells in the presence or absence of 10 ng/mL of VEGF. The cells are then removed from the culture flasks and lysed for 20 minutes over ice in lysis buffer containing 50 nM Hepes, pH 7.4, 75 mM NaCl, 1 mM EDTA, 1% Nonidet P-40 and 0.01% of SDS. The insoluble material is removed by centrifugation and 50 μg/mL of protein extract are separated by polyacrylamide gel electrophoresis containing sodium dodecyl sulfate (SDS) under denaturing conditions. The proteins are then transferred from the gel onto a nitrocellulose membrane (Amersham Pharmacia Biotech, Orsay) using a transfer apparatus (semi-dry transfer, Bio-Rad, Irvy-surSeine, France). The membrane is then incubated with primary antibodies to p42/p44 then coupled secondaries to peroxidase. Examination is done using the ECLplus system (Amersham Pharmacia Biotech, Orsay). The results are quantified using the Image Quant program (Molecular Dynamics).

By way of example, the P11 (cyclic) peptide strongly inhibits phosphorylation of p42/p44. The linear peptide has no effect (Table 3).

TABLE 3

| | Proliferation (IC50) | Migration (IC50) | p42 Phosphorylation (% Inhibition) | p44 Phosphorylation (% Inhibition) |
|---|---|---|---|---|
| P11 | 7 μM | 30 μM | 75% | 90% |
| P11 | >300 μM | >300 μM | 0% | 0% |

Table 3 shows the effect of the P11 peptide on cellular proliferation and migration and on phosphorylation of the MAP kinases (p42 and p44). The assays were done as indicated. Inhibition of phosphorylation and migration is indicated in inhibition values at 50% of the biological effect (IC50). 50 μM of peptides were used for the phosphorylation assays. The degree of phosphorylation is estimated after quantification of the signals obtained using autoradiographic films and the results are expressed in percent inhibition relative to the signal obtained using 10 ng/mL of VEGF alone.

The cyclopeptides of the invention can be used for producing angiogenesis inhibitor or activator systems either in soluble form or by coupling them to suitable supports.

FIG. 3 shows the first embodiment of an inhibitor system according to the invention.

In this figure, it can be seen that the cyclopeptide is coupled to a suitable support 1 by means of an organic spacer arm 3 which can comprise a moiety 4 capable of being cut by an enzyme system.

The organic spacer arm can be comprised of a hydrocarbon, fluorocarbon, polyether, polyethylene glycol, polyamine, polyamide, polyester, polysiloxane chain or a combination of these that is functionalized at each end in order to form a covalent bond on the one hand with the cyclopeptide and on the other hand with the support 1.

The moiety 4 capable of being cut by an enzyme system present in the spacer arm 3 can be particularly a peptide sequence that is a substrate of the enzymes such as the metalloproteases of the extra-cellular matrix.

The presence of this moiety thus enables releasing the cyclopeptide at the desired location when it is in contact with the appropriate enzymes, thus making it possible for the cyclopeptide to fulfill its function of inhibition of bonding of the VEGF to the KDR receptor and controlling angiogenesis.

FIG. 3 shows a [singles] *single* cyclopeptide bound to the support. Of course, supports can be used that comprise a large number of cyclopeptides, each one bound to the support by an organic spacer arm with or without such a moiety 4.

Figure 4:
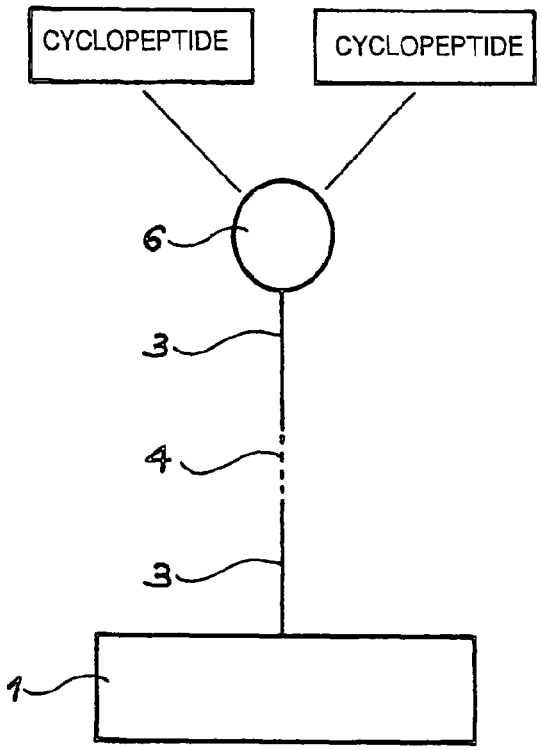
FIG. 4 represents fixation of an organic compound carrying two cyclopeptides onto a support by means of a spacer arm.

FIG. 4 shows a further embodiment of the systems of the invention in which two cyclopeptides are used for obtaining an activator effect on the KDR receptors.

In this case, two cyclopeptides are affixed by a compound 6 which is itself bound to the support 1 by an organic spacer arm 3; this arm can also comprise a moiety 4 capable of being cut by an enzyme system.

The choice of organic compound onto which the two cyclopeptides are attached allows them to be disposed in a satisfactory configuration for allowing dimerization of the vascular endothelium growth factor receptors.

Accordingly, the distance between the two fixed cyclopeptides is such that when the system is brought into contact with cells expressing VEGF receptors, it allows dimerization of said receptors.

The organic spacer arm 3 can be of the same type as that of FIG. 3 and comprise a moiety 4 of the same type as that of FIG. 3.

The organic compound 6 can be formed of hydrophilic-hydrophobic alternated sequences of the polyethylene glycol/alkane or fluoroalkane in order to enable appropriate disposition of the two cyclopeptides. Attachment of each cyclopeptide on said compound involves amine or carboxylic acid functions of the side chains of the cyclopeptide or acrylic type functions.

The support 1 used in the different embodiments of the systems of the invention can be in solid form or gel form. It can be an organic or inorganic solid.

Preferably, the support is an optionally biocompatible, biodegradable organic peptide. [The] *In* this case, attachment of the organic spacer arm on said polymer can be done by chemical or radiochemical means. In this latter case, the organic polymer support is subjected to irradiation by means of ionizing, plasma or photons beams on defined zones of the support that are intended to receive the spacer arm and the organic spacer arm is then subsequently grafted to those zones either directly or with the aid of a polymerizable monomer by a radical route (radiografting) comprising, for example, amine or carboxylic acid functions.

Coupling of the polymer, radiografted or not, is done, for example, by creation of amide bonds either between the carboxylic acid functions and the amine functions introduced at the end of the spacer arms or between the amine functions of the support and the carboxylic acid functions introduced at the ends of the spacer arms.

The following examples illustrate the production of such systems.

EXAMPLE 1

Production of a System Comprising Two Cyclopeptides Bonded Covalently by an Organic Compound.

Starting with an organic compound comprising three functional groups, one of which is protected:

$$\text{HOOC CH}_2\text{CH}_2\text{O(CH}_2\text{CH}_2\text{O)}_5\text{(CH}_2\text{)}_3\text{NH (CH}_2\text{CH}_2\text{O)}_5\text{CH}_2\text{CH}_2\text{ COOH} \qquad \text{(Compound 1)}$$

The spacer arm is attached to the NH group of this compound, and it corresponds to the formula:

$$\text{CH}_2{=}\text{CH—CO—NH—(CH}_2\text{)}_5\text{—CO—P—CO} \qquad \text{(Compound 2)}$$

wherein P represents the peptide that is a substrate of the metalloprotease of the extra-cellular matrix.

The organic compound 1 is prepared in the following steps:

Step N° 1

Condensation of Hexaethylene Glycol on Tertiobutyl Acrylate.

For this step, the operational procedure described by O. Seitz, H. Kunz, J. Org. Chem., 62, 813 (1997) [12] is followed:

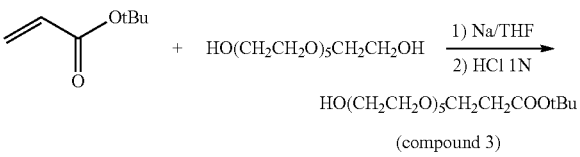

In a three-necked flask, the anhydrous THF is mixed with the hexaethylene glycol under nitrogen and while stirring. Then Na is added and allowed to dissolve. The tertiobutyl acrylate is then added. This is turned for 20 hours at room temperature. HCl is added in order to neutralize the solution. The THF is evaporated under reduced pressure, then the solution is flooded with saturated saline solution. The solution is then extracted three times using ethyl acetate. The entire organic phase is again flooded in saturated saline solution. The organic phase is collected and the ethyl acetate evaporated. The pure product (Compound 3) is recovered with a yield of 96%.

Step N° 2

Functionalizing of the Other End of Compound 3 by Azidation.

a) tosylation according to the operational procedure described by D. S. Wilbur et al., Bioconjugate Chem., 9, 813 (1998) [13]:

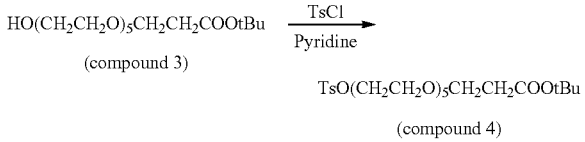

The pyridine and the starting Compound 3 are placed in a two-necked flask. The entirety is placed at 0° C. under $N_2$. Then the TsCl is added. After 15 hours of reaction, the solution is flooded in ice and extracted 3 times using $CH_2Cl_2$. The organic phase is washed with a solution of 2% acetic acid, then with water. The organic phase is then collected, dried over $MgSO_4$ and evaporated under reduced pressure. The product is purified by passage over a silica column (70/230) with 100% ethyl acetate used as the eluant. The product (Compound 4) is collected with a yield of 65%.

b) Azidation according to the operational procedure described by K. D. Reynolds, Bioconjugate Chem., 10, 1021-31 (1999) [14]:

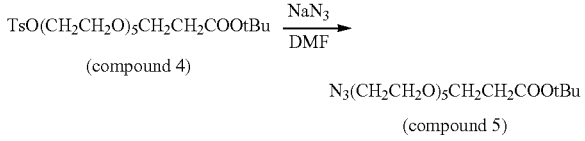

The Compound 4 with some DMF is placed in a two-necked flask under $N_2$, then $NaN_3$ is added. It is turned for 20 hours; the solution becomes opaque. The solution is passed over a frit, then the DMF is coevaporated with toluene. A white precipitate is obtained that is diluted with ether. The solution is again passed over the frit and the ether is evaporated.

Thus Compound 5 is obtained with a yield of 95%.

Step N° 3

Functionalizing of the Other End of Compound 3 by Allylation.

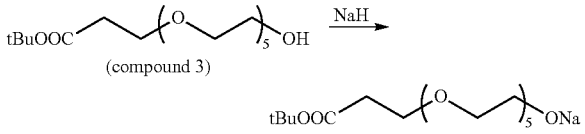

Allylaton is performed by nucleophilic substitution of commercial allyl bromide by the sodium salt of hexaethylene glycol. The derivative obtained is

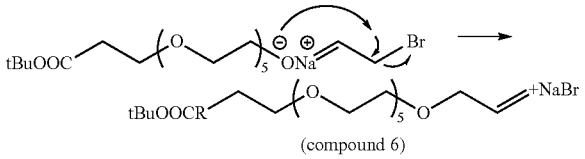

(compound 6)

then isolated by chromatography over a silica column with a yield of 50%.

Synthesis is done in THF.

Step N° 4

Hydroboration.

This is done according to the method described by Carboni et al, J. Org. Chem., 1993, 58, 3736-3741 [15] by reacting Compound 5 with Compound 6 to which dichloroborane has been added. Compound 7 is obtained.

$tBuOOCCH_2CH_2O(CH_2CH_2)_5CH_2\ CH_2CH_2HN$
$(CH_2CH_2O)_5CH_2CH_2$—COOtBu (compound 7)

Step N° 5

Protection of the Nitrogen.

Compound 7 is treated with FmocOSu according to the method used by Chetyrkina et al., Tetrahedron Letters 2000, 41, 1923-1926 [16], for example.

Compound 8 is obtained.

(compound 8)

Fmoc
|
$tBuOOCCH_2CH_2O(CH_2CH_2O)_5CH_2CH_2CH_2N(CH_2CH_2O)_5CH_2CH_2COOtBu$

Step N° 6

Deprotection of the Tertiobutyloxy Carbonyle Groups.

Compound 8, to which the anisol has been added, is placed in a two-necked flask and then the TFA. The reaction is allowed to turn for 1 h 30 minutes at 25° C., then the TFA is evaporated under reduced pressure. The crude is then passed over a silica column (70/230) using 95/5 $CH_2Cl_2$/MeOH, then 90/10 $CH_2Cl_2$/MeOH as the eluent. Pure compound 9 is then collected with a yield of 65%.

(compound 9)

Fmoc
|
$HOOCCH_2CH_2O(CH_2CH_2O)_5CH_2CH_2CH_2N(CH_2CH_2O)_5CH_2CH_2COOH$

The P23 cyclopeptides are attached to the two functional groups (COOH) of Compound 9 by proceeding in the following manner.

The Compound 9 is placed in solution in some THF and then activated by means of N,N-dimethylpropyl, ethyl carbodiimide.

Then a quantity corresponding to the molar equivalent of each cyclopeptide is added and the mixture is left for a period of 12 hours at room temperature, then lyophilized. The lyophilysate is collected using chloroform, the urea is eliminated that is formed by filtration and the filtrate is evaporated under reduced pressure.

The product obtained is identified by infrared spectrometry using Fourier transformation, RMN of the proton and mass spectrometry. It corresponds to the desired product.

In order to assure fixation of this product on a support, at the very beginning a spacer arm is attached to the NH group, said spacer aim comprising a polymerizable function. One then proceeds as follows Deprotection of the NH Group.

Firstly deprotection of the NH group of compound 9 is carried out by treatment with piperidine.

Besides, the spacer arm is being prepared by carrying out the following reaction:

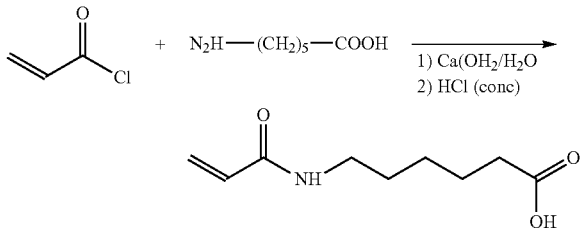

(compound 10)

The salt and the water are placed in a three-necked flask, then the $H_2N$ $(CH_2)_5$—COOH amino acid; the entire mixture is cooled to 0° C. While agitating briskly, the acrylic acid chloride is added at a rate of around 3 mL per minute.

It is allowed to turn for 10 minutes at room temperature, then the solution is passed over a frit. The flask is brought again to 0° C. under brisk agitation. Then the concentrated HCl is added to obtain a pH=2. This provokes precipitation of the product. The mixture is then filtered and the dried product (Compound 10) is pure.

The yield is 75%.

Condensation of Compound 10

Compound 10 is condensed over the peptide P which is the substrate of the metalloproteases of the extra-cellular matrix at the time of the last step of its synthesis on solid phase, then the entirety is freed from the resin without deprotection of the side chains.

The molecule obtained is then condensed using dicyclohexyl carbodiimide over the deprotected Compound 9. Then the side chains of the peptide of the spacer arm are deprotected, then the arm is attached onto the polymer support with the aid of the acrylic functions of the arm.

An industrial film made of ethylene polyterephthalate with a 25 μm thickness is used as the support and it is previously extracted using the Soxhlet using reflux toluene at a temperature of 110° C. over a period of 12 hours, in order to eliminate any trace of organic monomer.

A nickel or copper metallic grid having a thickness of approximately 50 μm is then placed on the polymer film, said grid is pierced with circular holes having a diameter of from 5 to 10 μm regularly distributed over its entire surface with an interval of approximately 100 μm. The grid has been manufactured by electroforming in order to have perfect reproducibility and a very high precision of the order of a micrometer.

Then the polymer film is then subjected to irradiation by means of electron beam for irradiation only the zones corresponding to the holes of the grid. The electron beam has the following characteristics:

energy Ep=2.5 MeV maximal intensity Imax=1 μA maximal dose=500 kGy.

Irradiation is done in an oxygen-containing atmosphere.

After irradiation, the grid is removed from the polymer film and the irradiated polymer film is placed in contact with the organic compound, on which the two cyclopeptides are attached for grafting this compound with the aid of the spacer arm onto the polymer film. This fixation is done by placing the film in contact with a $10^{-2}$ M solution of the organic compound previously obtained by working at 40° C.

Thus, the organic compound is grafted by the acrylic functions of the spacer arm onto the irradiated zones of the polymer film.

The final product is characterized by FT-IR and spectrometry and XPS.

EXAMPLE 2

Production of a System Comprising Two Cyclopeptides.

In this example, the same operational procedure is followed as previously used in the above example for coupling the two P23 cyclopeptides on two functions of the organic compound described.

In order to perform this coupling, the organic compound is put into solution in some chloroform and activated using dicyclohexyl carbodiimide [DCCI] *DCCI*, then a quantity is added corresponding to 1 molar equivalent of each cyclopeptide and the reaction environment is maintained at 4° C. over a period of 12 hours. The precipitate of dicyclohexylurea is removed by filtration, then the filtrate is evaporated under reduced pressure.

The product obtained is characterized by infrared spectrometry using Fourier transformation, proton RMN and mass spectrometry, as previously done.

The a spacer arm is attached to the NH group of the organic compound as in Example 1.

The assembly is then attached to a support comprised of an 25 μm thick industrial film made of poly (vinylidene fluoride/hexafluoropropylene) PVDF/HFP. The film is previously subjected to extraction on the Soxhlet in some reflux dichloromethane at a temperature of 40° C. for 12 hours in order to eliminate any trace of organic monomer.

The film is then subjected to irradiation under air by accelerated heavy ions. The ions used are oxygen ions haven a primary energy Ep of around 10 MeV/uma at fluences of between $10^7$ and $10^9$ ions/cm$^2$ and at intensities of the order of $10^2$ to $5\times10^2$ nA. Operation at low fluence was chosen in such a way that there was no recovery of latent traces.

This operation is determined directly by the irradiation parameters (atomic number of the ion, primary energy, fluence). In this case, the random distribution of the active centers in the disturbed zone created at the time of irradiation (emergence of latent traces) allows radiografting by means of two organic spacer arms each carrying a cyclopeptide by blocking the distance between the anchoring points in such a way that the distance d between two cyclopeptides favors dimerization of the VEGF receptors.

The irradiated zones are used for grafting organic spacer arms carrying the cyclopeptides obtained as described above, by reaction of their acrylic type function with the irradiated support, by virtue of free radicals created along the latent trace of the ion and the emergence of same at the surface of the polymer film.

This coupling is done by heating the irradiated film, placed in the presence of a $10^{-3}$ M solution of the organic arms carrying the cyclopeptides, to 40° C. in tetrahydrofurane.

The final compound is characterized using FT-IR spectrometry and XPS.

CITED DOCUMENTS

[1]: Ferrara el al, Nature Medicine, vol. 5, n°12, Décembre 1999, pages. 1361-1364.

[2]: Hagedorn et Bikfalvi, Critical Reviews in Oncology/Hematology, 34, 2000, pages 89-110.

[3]: Muller Y. A., Structure, 1997, 5, n°10, pages 1325-1338.

[4]: Presla et al, Cancer Research, 57 1997, pages 4593-4599.

[5]: Ortega et al, Am. J. Pathol. November 1997, 11 (5), pages 1215-1224.

[6]: Piossck et al, The Journal of Biological Chemistry, vol. 274, n°, 1999, pages 5612-5619.

[7]: Fairbrother et al, Biochemisty 37, 1998, pages 17754-17764.

[8]: U.S. Pat. No. 5,939,383

[9]: Bekele et al, J. Org. Chem. 62, 1997, pages 2259-2262.

[10]: Binétruy-Tournaire et al, EMBO Journal, 19, (7), 2000, pages 1525-1533.

[11]: Jonca et al, J. Biol. Chem., 1997, 272, pages 24203.

[12]: O. Seitz, H. Kunz, J. Org. Chem., 62, 813 (1997).

[13]: Wilbur et al, Bioconjugate Chem., 9, 813 (1998).

[14]: J. K. D. Reynolds, Bioconjugate Chem., 10, 1021-31 (1999).

[15]: Carboni et al, J. Org. Chem., 1993, 58, pages 3736-3741.

[16]: Chetyrkina et al, Tetrahedron Letters, 2000, 41, pages 1 923-1 926.

[17]: Sato et Rifkin (J. Cell Biol., September, 1988, (107 (3): 1199-205).

TABLE 1

| | | |
|---|---|---|
| SEQ ID NO: 14 | P1 | H-Arg-Ile-Lys-Pro-His-OH |
| SEQ ID NO: 15 | P2 | H-Gln-Ile-Met-Arg-Ile-Lys-Pro-His-OH |
| SEQ ID NO: 16 | P3 | H-Arg-Ile-Lys-Pro-His-Gln-Gly-OH |
| SEQ ID NO: 17 | P4 | H-Gln-Ile-Met-Arg-Ile-Lys-Pro-His-Gln-Gly-Gln-His-Ile-Gly-Glu-OH |
| SEQ ID NO: 18 | P5 | H-Gln-Ile-Met-Arg-Ile-Lys-Pro-His-Gln-Gly-Gln-His-Ile-Gly-OH |
| SEQ ID NO: 19 | P6 | H-Gly-Arg-Ile-Lys-DPro-His-Gln-Gly-Gln-His-OH |
| SEQ ID NO: 2 | P7 | cyclo(Gly-Arg-Ile-Lys-DPro-His-Gln-Gly-Gln-His) |
| SEQ ID NO: 3 | P8 | cyclo(Gly-Arg-Ile-Lys-Pro-His-Gln-Gly-His) |
| SEQ ID NO: 4 | P9 | cyclo(Pro-Arg-Ile-Lys-Pro-His-Gln-Gly-Gln-His) |
| SEQ ID NO: 20 | P10 | H-Gln-Ile-Met-Arg-Ile-Lys-Pro-His-Gln-Gly-Gln-His-Ile-Gly-Glu-Oallyle |

TABLE 1-continued

| | | |
|---|---|---|
| SEQ ID NO: 5 | P11 | cyclo(DPhe-Pro-Gln-Ile-Met-Arg-Ile-Lys-Pro-His-Gln-Gly-Gln-His-Ile-Gly-Glu) |
| SEQ ID NO: 6 | P12 | cyclo(Gly-Gln-Ile-Met-Arg-Ile-Lys-Pro-His-Gln-Gly-Gln-His-Ile-Gly-Glu) |
| SEQ ID NO: 7 | P13 | cyclo(Pro-Gln-Ile-Met-Arg-Ile-Lys-Pro-His-Gln-Gly-Gln-His-Ile-Gly-Glu) |
| SEQ ID NO: 21 | P14 | H-Pro-Gln-Ile-Met-Arg-Ile-Lys-Pro-His-Gln-Gly-Gln-His-Ile-Gly-Glu-OH |
| SEQ ID NO: 22 | P15 | H-Gly-Gln-Ile-Met-Arg-Ile-Lys-Pro-His-Gln-Gly-Gln-His-Ile-Gly-Glu-OH |
| SEQ ID NO: 8 | P16 | cyclo(Arg-Ile-Lys-Pro-His-Gln-Gly) |
| SEQ ID NO: 9 | P17 | cyclo(Pro-Arg-Ile-Lys-Pro-His-Gln-Gly) |

TABLE 1-continued

| | | |
|---|---|---|
| SEQ ID NO: 23 | P18 | cyclo(DPhe-Arg-Ile-Lys-Pro-His-Gln) |
| SEQ ID NO: 10 | P19 | cyclo(Gln-Ile-Met-Arg-Ile-Lys-Pro-His-Gln-Gly-Gln-His-Ile-Gly-Glu) |
| SEQ ID NO: 11 | P20 | cyclo(DPhe-Pro-Gln-Ile-Met-Arg-Ile-Lys-Pro-His-Gln-Gly-Gln-His-Ile-Gly) |
| SEQ ID NO: 12 | P21 | cyclo(DPhe-Pro-Ile-Met-Arg-Ile-Lys-Pro-His-Gln-Gly-Gln-His-Ile) |
| SEQ ID NO: 24 | P22 | cyclo(Glu-Gln-Ile-Met-Arg-Ile-Lys-Pro-His-Gln) |
| SEQ ID NO: 13 | P23 | cyclo(DTyr-Pro-Arg-Ile-Lys-Pro-His-Gln) |
| SEQ ID NO: 25 | P24 | cyclo(Gly-Arg-Ile-Lys-Pro-His) |

TABLE 2

| Peptide | $VEGF_{165}$ amino acid sequence | Number of amino acids | Synthesis Method | Molecular weight [calculée] *calculated* | Molecular weight [trouvée] *found* | $IC_{50}$ (μM) |
|---|---|---|---|---|---|---|
| P1 | 82-86 | 5 | | 649.8 | 650.3 | >300.0 |
| P2 | 79-86 | 8 | | 1022.3 | 1022.1 | >300.0 |
| P3 | 82-88 | 7 | | 835.0 | 836.6 | >300.0 |
| P4 | 79-93 | 15 | | 1772.1 | 1773.3 | >300.0 |
| P5 | 79-92 | 14 | | 1642.9 | 1644.1 | >300.0 |
| P6 | $Gly^{81}$-82-90-$DPro^{85}$ | 10 | | 1157.3 | 1158.4 | >300.0 |
| P7 | ($Gly^{81}$-82-90)$DPro^{85}$ | 10 | A | 1139.3 | 1139.9 | >300.0 |
| P8 | ($Gly^{81}$-82-88-$His^{89}$) | 9 | A | 1011.2 | 1012.0 | 200.0 |
| P9 | ($Pro^{81}$-82-90) | 10 | A | 1179.6 | 1180.6 | 300.0 |
| P10 | 79-93-Oallyle | 15 | | 1821.1 | 1813.1 | >300.0 |
| P11 | ($DPhe^{77}$-$Pro^{78}$-79-93) | 17 | A | 1998.3 | 1998.7 | 2.0 |
| P12 | ($Gly^{78}$-79-93) | 16 | A, B | 1811.1 | 1813.1 | 300.0 |
| P13 | ($Pro^{78}$-79-93) | 16 | A, B | 1851.2 | 1851.4 | >300.0 |
| P14 | $Pro^{78}$-79-93 | 16 | | 1869.2 | 1869.0 | >300.0 |
| P15 | $Gly^{78}$-79-93 | 16 | | 1829.1 | 1828.5 | >300.0 |
| P16 | (82-88) | 7 | A | 817.0 | 817.9 | 32.0 |
| P17 | ($Pro^{81}$-82-88) | 8 | A | 914.1 | 915.6 | 10.0 |
| P18 | ($DPhe^{81}$-82-87) | 7 | A | 1004.2 | 1004.7 | >300.0 |
| P19 | (79-93) | 15 | B | 1754.0 | 1755.0 | 5.0 |
| P20 | ($DPhe^{77}$-$Pro^{78}$-79-92) | 16 | B | 1869.2 | 1869.7 | 10.0 |
| P21 | ($DPhe^{78}$-$Pro^{79}$-80-91) | 14 | B | 1684.0 | 1685.4 | 200.0 |
| P22 | ($Glu^{78}$-79-87) | 10 | B | 1261.5 | 1262.7 | >300.0 |
| P23 | ($DTyr^{80}$-$Pro^{81}$-82-87) | 8 | A | 1020.2 | 1021.7 | 8.0 |
| P24 | ($Gly^{81}$-82-86) | 6 | A | 688.8 | 689.9 | 8.0 |

SEQUENCE LISTING

```
<160> NUMBER OF SEQ ID NOS: 30

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ile Lys Pro His Gln Gly
1               5
```

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide
<220> FEATURE:
<221> NAME/KEY: MOD_RES
<222> LOCATION: (5)..(5)
<223> OTHER INFORMATION: D-Pro

<400> SEQUENCE: 2

Gly Arg Ile Lys Xaa His Gln Gly Gln His
1 5 10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide

<400> SEQUENCE: 3

Gly Arg Ile Lys Pro His Gln Gly His
1 5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide

<400> SEQUENCE: 4

Pro Arg Ile Lys Pro His Gln Gly Gln His
1 5 10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide
<220> FEATURE:
<221> NAME/KEY: MOD_RES
<222> LOCATION: (1)..(1)
<223> OTHER INFORMATION: D-Phe

<400> SEQUENCE: 5

Xaa Pro Gln Ile Met Arg Ile Lys Pro His Gln Gly Gln His Ile Gly
1 5 10 15

Glu

<210> SEQ ID NO 6
<211> LENGTH: 16
<212> TYPE: PRT
<213> ORGANISM: Artificial Sequence <220> FEATURE:
<223> OTHER INFORMATION: Description of Artificial Sequence: Synthetic
peptide
<220> FEATURE:
<223> OTHER INFORMATION: Cyclic peptide

<400> SEQUENCE: 6

Gly Gln Ile Met Arg Ile Lys Pro His Gln Gly Gln His Ile Gly Glu
1 5 10 15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide

<400> SEQUENCE: 7

Pro Gln Ile Met Arg Ile Lys Pro His Gln Gly Gln His Ile Gly Glu
1 5 10 15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide

<400> SEQUENCE: 8

Arg Ile Lys Pro His Gln Gly
1 5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide

<400> SEQUENCE: 9

Pro Arg Ile Lys Pro His Gln Gly
1 5

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide

<400> SEQUENCE: 10

Gln Ile Met Arg Ile Lys Pro His Gln Gly Gln His Ile Gly Glu
1 5 10 15

<210> SEQ ID NO 11
<211> LENGTH: 16
<212> TYPE: PRT
<213> ORGANISM: Artificial Sequence <220> FEATURE:
<223> OTHER INFORMATION: Description of Artificial Sequence: Synthetic
peptide
<220> FEATURE:
<223> OTHER INFORMATION: Cyclic peptide
<220> FEATURE:
<221> NAME/KEY: MOD_RES
<222> LOCATION: (1)..(1)
<223> OTHER INFORMATION: D-Phe

<400> SEQUENCE: 11

Xaa Pro Gln Ile Met Arg Ile Lys Pro His Gln Gly Gln His Ile Gly
1 5 10 15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide
<220> FEATURE:
<221> NAME/KEY: MOD_RES
<222> LOCATION: (1)..(1)
<223> OTHER INFORMATION: D-Phe

<400> SEQUENCE: 12

Xaa Pro Ile Met Arg Ile Lys Pro His Gln Gly Gln His Ile
1 5 10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide
<220> FEATURE:
<221> NAME/KEY: MOD_RES
<222> LOCATION: (1)..(1)
<223> OTHER INFORMATION: D-Tyr

<400> SEQUENCE: 13

Xaa Pro Arg Ile Lys Pro His Gln
1 5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Arg Ile Lys Pro His
1 5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

```
Gln Ile Met Arg Ile Lys Pro His
1               5


<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ile Lys Pro His Gln Gly
1               5


<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ile Met Arg Ile Lys Pro His Gln Gly Gln His Ile Gly Glu
1               5                   10                  15


<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ile Met Arg Ile Lys Pro His Gln Gly Gln His Ile Gly
1               5                   10


<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Arg Ile Lys Pro His Gln Gly Gln His
1               5                   10


<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ile Met Arg Ile Lys Pro His Gln Gly Gln His Ile Gly Glu
1               5                   10                  15


<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 21

Pro Gln Ile Met Arg Ile Lys Pro His Gln Gly Gln His Ile Gly Glu
1 5 10 15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Gly Gln Ile Met Arg Ile Lys Pro His Gln Gly Gln His Ile Gly Glu
1 5 10 15

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide
<220> FEATURE:
<221> NAME/KEY: MOD_RES
<222> LOCATION: (1)..(1)
<223> OTHER INFORMATION: D-Phe

<400> SEQUENCE: 23

Xaa Arg Ile Lys Pro His Gln
1 5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide

<400> SEQUENCE: 24

Glu Gln Ile Met Arg Ile Lys Pro His Gln
1 5 10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide

<400> SEQUENCE: 25

Gly Arg Ile Lys Pro His
1 5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Gly Pro Gln Gly Leu Leu Gly Ala
1 5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide
<220> FEATURE:
<221> NAME/KEY: MOD_RES
<222> LOCATION: (1)..(1)
<223> OTHER INFORMATION: D-Phe or D-Tyr

<400> SEQUENCE: 27

Xaa Pro Gln Ile Met Arg Ile Lys Pro His Gln Gly Gln His Ile Gly
1 5 10 15

Glu

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Cyclic peptide
<220> FEATURE:
<221> NAME/KEY: MOD_RES
<222> LOCATION: (1)..(1)
<223> OTHER INFORMATION: D-Phe or D-Tyr

<400> SEQUENCE: 28

Xaa Pro Gln Ile Met Arg Ile Lys Pro His Gln Gly Gln His Ile Gly
1 5 10 15

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: D-Pro

<400> SEQUENCE: 29

Gly Arg Ile Lys Xaa His Gln Gly Gln His
1 5 10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Gln Ile Met Arg Ile Lys Pro His Gln Gly Gln His Ile Gly Glu
1 5 10 15

The invention claimed is:

1. A cyclopeptide chosen from among the following compounds:

```
P11: cyclo(DPhe-Pro-Gln-Ile-Met-  SEQ ID NO: [5] 27
     Arg-Ile-Lys-Pro-His-Gln-
     Gly-Gln-His-Ile-Gly-Glu)

P16: cyclo(Arg-Ile-Lys-Pro-His-   SEQ ID NO: 8
     Gln-Gly)

P17: cyclo(Pro-Arg-Ile-Lys-Pro-   SEQ ID NO: 9
     His-Gln-Gly)

P19: cyclo(Gln-Ile-Met-Arg-Ile-   SEQ ID NO: 10
     Lys-Pro-His-Gln-Gly-Gln-His-
     Ile-Gly-Glu)

P20: cyclo(DPhe-Pro-Gln-Ile-Met-  SEQ ID NO: [11] 28
     Arg-Ile-Lys-Pro-His-Gln-Gly-
     Gln-His-Ile-Gly)

P23: cyclo(DTyr-Pro-Arg-Ile-Lys-  SEQ ID NO: 13
     Pro-His-Gln)

P24: cyclo(Gly-Arg-Ile-Lys-Pro-   SEQ ID NO: 25
     His)
```

and the compounds P11 and P20, wherein DPhe is replaced by DTyr.

2. A pharmaceutical composition for inhibiting angiogenesis comprising a cyclopeptide chosen among the following cyclopeptides:

```
P11: cyclo(DPhe-Pro-Gln-Ile-Met-  SEQ ID NO: [5] 27
     Arg-Ile-Lys-Pro-His-Gln-Gly-
     Gln-His-Ile-Gly-Glu)

P16: cyclo(Arg-Ile-Lys-Pro-His-   SEQ ID NO: 8
     Gln-Gly)

P17: cyclo(Pro-Arg-Ile-Lys-Pro-   SEQ ID NO: 9
     His-Gln-Gly)

P19: cyclo(Gln-Ile-Met-Arg-Ile-   SEQ ID NO: 10
     Lys-Pro-His-Gln-Gly-Gln-His-
     Ile-Gly-Glu)

P20: cyclo(DPhe-Pro-Gln-Ile-Met-  SEQ ID NO: [11] 28
     Arg-Ile-Lys-Pro-His-Gln-Gly-
     Gln-His-Ile-Gly)

P23: cyclo(DTyr-Pro-Arg-Ile-Lys-  SEQ ID NO: 13
     Pro-His-Gln)

P24: cyclo(Gly-Arg-Ile-Lys-Pro-   SEQ ID NO: 25
     His)
```

and the cyclopeptides P11 and P20, wherein DPhe is replaced by DTyr.

3. A pharmaceutical composition for activating angiogenesis comprising two identical or different cyclopeptides, coupled [with] *to* a pharmaceutically acceptable organic compound, the cyclopeptides being chosen from among the following cyclopeptides:

```
P11: cyclo(DPhe-Pro-Gln-Ile-Met-  SEQ ID NO: [5] 27
     Arg-Ile-Lys-Pro-His-Gln-Gly-
     Gln-His-Ile-Gly-Glu)

P16: cyclo(Arg-Ile-Lys-Pro-His-   SEQ ID NO: 8
     Gln-Gly)

P17: cyclo(Pro-Arg-Ile-Lys-Pro-   SEQ ID NO: 9
     His-Gln-Gly)
```

-continued

```
P19: cyclo(Gln-Ile-Met-Arg-Ile-   SEQ ID NO: 10
     Lys-Pro-His-Gln-Gly-Gln-His-
     Ile-Gly-Glu)

P20: cyclo(DPhe-Pro-Gln-Ile-Met-  SEQ ID NO: [11] 28
     Arg-Ile-Lys-Pro-His-Gln-Gly-
     Gln-His-Ile-Gly)

P23: cyclo(DTyr-Pro-Arg-Ile-Lys-  SEQ ID NO: 13
     Pro-His-Gln)

P24: cyclo(Gly-Arg-Ile-Lys-Pro-   SEQ ID NO: 25
     His)
```

and the cyclopeptides P11 and P20, wherein DPhe is replaced by DTyr.

4. [The] *A* system comprising a cyclopeptide according to claim 1, covalently bound to an organic spacer arm.

5. The system according to claim 4, wherein the organic spacer arm is covalently bound to a support.

6. A system comprising two cyclopeptides according to 1 covalently bound to an organic compound.

7. The system according to claim 6, wherein the distance between the two cyclopeptides is such that, when the system is brought into contact with cells expressing vascular endothelium growth factor (VEGF) receptors, it allows dimerization of said receptors.

8. The system according to claim 6, wherein the organic compound is covalently bound to a support [with the aid of] *via* an organic spacer arm.

9. The system according to claim 7, wherein the organic compound is covalently bound to a support [with the aid of] *via* an organic spacer arm.

10. A system comprising a [solid] support [upon where upon] *and one or more* cyclopeptides according to claim 1, *wherein each of the one or more cyclopeptides* are attached by covalent bonding[, each of said cyclopeptides being bound] to the support [by] *via* an organic spacer arm, *and wherein the support is in solid form or gel form.*

11. The system according to claim 4, wherein the *organic* spacer arm comprises a hydrocarbon, *a* fluorocarbon, *a* polyether, *a* polyethylene glycol, *a* polyamine, *a* polyamide, *a* polyester, *a* polysiloxane chain or a combination [of these that] *thereof, and wherein the organic spacer arm* is functionalized [at each end] *on one end* for forming a covalent bond [on the one hand] with the cyclopeptide and [on the other hand] *is functionalized on another end for forming a covalent bond* with the support.

12. The system according to claim 5, wherein the *organic* spacer arm comprises a hydrocarbon, *a* fluorocarbon, *a* polyether, *a* polyethylene glycol, *a* polyamine, *a* polyamide, *a* polyester, *a* polysiloxane chain or a combination [of these that] *thereof, and wherein the organic spacer arm* is functionalized [at each] *on one* end for forming a covalent bond [on the one hand] with the cyclopeptide and [on the other hand] *is functionalized on another end for forming a covalent bond* with the support.

13. The system according to claim 6, wherein the *organic* spacer arm comprises a hydrocarbon, *a* fluorocarbon, *a* polyether, *a* polyethylene glycol, *a* polyamine, *a* polyamide, *a* polyester, *a* polysiloxane chain or a combination [of these that] *thereof, and wherein the organic spacer arm* is functionalized [at each] *on one* end for forming a covalent bond [on the one hand] with the cyclopeptide and [on the other hand] *is functionalized on another end for forming a covalent bond* with the support.

14. The system according to claim 7, wherein the *organic* spacer arm comprises a hydrocarbon, *a* fluorocarbon, *a* polyether, *a* polyethylene glycol, *a* polyamine, *a* polyamide, *a* polyester, *a* polysiloxane chain or a combination [of these that] *thereof, and wherein the organic spacer arm* is functionalized [at each] *on one* end for forming a covalent bond [on the one hand] with the cyclopeptide and [on the other hand] *is functionalized on another end for forming a covalent bond* with the support.

15. The system according to claim 8, wherein the *organic* spacer arm comprises a hydrocarbon, *a* fluorocarbon, *a* polyether, *a* polyethylene glycol, *a* polyamine, *a* polyamide, *a* polyester, *a* polysiloxane chain or a combination [of these that] *thereof, and wherein the organic spacer arm* is functionalized [at each] *on one* end for forming a covalent bond [on the one hand] with the cyclopeptide and [on the other hand] *is functionalized on another end for forming a covalent bond* with the support.

16. The system according to claim 9, wherein the *organic* spacer arm comprises a hydrocarbon, *a* fluorocarbon, *a* polyether, *a* polyethylene glycol, *a* polyamine, *a* polyamide, *a* polyester, *a* polysiloxane chain or a combination [of these that] *thereof, and wherein the organic spacer arm* is functionalized [at each] *on one* end for forming a covalent bond [on the one hand] with the cyclopeptide and [on the other hand] *is functionalized on another end for forming a covalent bond* with the support.

17. The system according to claim 10, wherein the *organic* spacer arm comprises a hydrocarbon, *a* fluorocarbon, *a* polyether, *a* polyethylene glycol, *a* polyamine, *a* polyamide, *a* polyester, *a* polysiloxane chain or a combination [of these that] *thereof, and wherein the organic spacer arm* is functionalized [at each] *on one* end for forming a covalent bond [on the one hand] with the cyclopeptide and [on the other hand] *is functionalized on another end for forming a covalent bond* with the support.

18. The system according to claim 4, wherein the organic spacer arm further comprises a moiety capable of being [cut] *cleaved* by an enzymatic system.

19. The system according to claim 5, wherein the organic spacer arm further comprises a moiety capable of being [cut] *cleaved* by an enzymatic system.

20. The system according to claim 6, wherein the organic spacer arm further comprises a moiety capable of being [cut] *cleaved* by an enzymatic system.

21. The system according to claim 7, wherein the organic spacer arm further comprises a moiety capable of being [cut] *cleaved* by an enzymatic system.

22. The system according to claim 8, wherein the organic spacer arm further comprises a moiety capable of being [cut] *cleaved* by an enzymatic system.

23. The system according to claim 9, wherein the organic spacer arm further comprises a moiety capable of being [cut] *cleaved* by an enzymatic system.

24. The system according to claim 10, wherein the organic spacer arm further comprises a moiety capable of being [cut] *cleaved* by an enzymatic system.

25. The system according to claim 11, wherein the organic spacer arm further comprises a moiety capable of being [cut] *cleaved* by an enzymatic system.

26. The system according to claim 12, wherein the organic spacer arm further comprises a moiety capable of being [cut] *cleaved* by an enzymatic system.

27. The system according to claim 13, wherein the organic spacer arm further comprises a moiety capable of being [cut] *cleaved* by an enzymatic system.

28. The system according to claim 14, wherein the organic spacer arm further comprises a moiety capable of being [cut] *cleaved* by an enzymatic system.

29. The system according to claim 15, wherein the organic spacer arm further comprises a moiety capable of being [cut] *cleaved* by an enzymatic system.

30. The system according to claim 16, wherein the organic spacer arm further comprises a moiety capable of being [cut] *cleaved* by an enzymatic system.

31. The system according to claim 17, wherein the organic spacer arm further comprises a moiety capable of being [cut] *cleaved* by an enzymatic system.

32. The system according to claim 11, wherein the organic spacer arm further comprises a bioactive compound.

33. The system according to claim 12, wherein the organic spacer arm further comprises a bioactive compound.

34. The system according to claim 13, wherein the organic spacer arm further comprises a bioactive compound.

35. The system according to claim 14, wherein the organic spacer arm further comprises a bioactive compound.

36. The system according to claim 15, wherein the organic spacer arm further comprises a bioactive compound.

37. The system according to claim 16, wherein the organic spacer arm further comprises a bioactive compound.

38. The system according to claim 17, wherein the organic spacer arm further comprises a bioactive compound.

39. The system according to claim 18, wherein the organic spacer arm further comprises a bioactive compound.

40. The system according to claim 19, wherein the organic spacer arm further comprises a bioactive compound.

41. The system according to claim 20, wherein the organic spacer arm further comprises a bioactive compound.

42. The system according to claim 21, wherein the organic spacer arm further comprises a bioactive compound.

43. The system according to claim 22, wherein the organic spacer arm further comprises a bioactive compound.

44. The system according to claim 23, wherein the organic spacer arm further comprises a bioactive compound.

45. The system according to claim 24, wherein the organic spacer arm further comprises a bioactive compound.

46. The system according to claim 25, wherein the organic spacer arm further comprises a bioactive compound.

47. The system according to claim 26, wherein the organic spacer arm further comprises a bioactive compound.

48. The system according to claim 27, wherein the organic spacer arm further comprises a bioactive compound.

49. The system according to claim 28, wherein the organic spacer arm further comprises a bioactive compound.

50. The system according to claim 29, wherein the organic spacer arm further comprises a bioactive compound.

51. The system according to claim 30, wherein the organic spacer arm further comprises a bioactive compound.

52. The system according to claim 31, wherein the organic spacer arm further comprises a bioactive compound.

53. The system according to claim 5, wherein the support is an organic or an inorganic solid.

54. The system according to claim 8, wherein the support is an organic or an inorganic solid.

55. The system according to claim 9, wherein the support is an organic or an inorganic solid.

56. The system according to claim 10, wherein the support is an organic or an inorganic solid.

57. The system according to claim 5, wherein the support is an organic polymer in solid form or gel form.

58. The system according to claim 8, wherein the support is an organic polymer in solid form or gel form.

59. The system according to claim 9, wherein the support is an organic polymer in solid form or gel form.

60. The system according to claim 10, wherein the support is an organic polymer in solid form or gel form.

61. The system according to claim 57, wherein the organic polymer is *a* biocompatible, biodegradable [polymer] or [a non biocompatible, non biodegradable] *non-biodegradable* polymer.

62. The system according to claim 58, wherein the organic polymer is *a* biocompatible, biodegradable [polymer] or [a non biocompatible, non biodegradable] *non-biodegradable* polymer.

63. The system according to claim 59, wherein the organic polymer is *a* biocompatible, biodegradable [polymer] or [a non biocompatible, non biodegradable] *non-biodegradable* polymer.

64. The system according to claim 60, wherein the organic polymer is *a* biocompatible, biodegradable [polymer] or [a non biocompatible, non biodegradable] *non-biodegradable* polymer.

65. The system according to claim 61, wherein the organic polymer is chosen from among ethylene polyterephthalate, the copolymers of vinylidene fluoride, and hexafluoro propylene, the polyvinyl alcohols, the polyhydroxyethyl methacrylates, the polysaccharides and their copolymers.

66. The system according to claim 62, wherein the organic polymer is chosen from among ethylene polyterephthalate, the copolymers of vinylidene fluoride, and hexafluoro propylene, the polyvinyl alcohols, the polyhydroxyethyl methacrylates, the polysaccharides and their copolymers.

67. The system according to claim 63, wherein the organic polymer is chosen from among ethylene polyterephthalate, the copolymers of vinylidene fluoride, and hexafluoro propylene, the polyvinyl alcohols, the polyhydroxyethyl methacrylates, the polysaccharides and their copolymers.

68. The system according to claim 64, wherein the organic polymer is chosen from among ethylene polyterephthalate, the copolymers of vinylidene fluoride, and hexafluoro propylene, the polyvinyl alcohols, the polyhydroxyethyl methacrylates, the polysaccharides and their copolymers.

[69. The system for activating angiogenesis according to claim 6, wherein the cyclopeptide is chosen from among the following cyclopeptides:

```
P11: cyclo(DPhe-Pro-Gln-Ile-Met-Arg- SEQ ID NO: 6
     Ile-Lys-Pro-His-Gln-Gly-Gln-
     His-Ile-Gly-Glu)

P16: cyclo(Arg-Ile-Lys-Pro-His-Gln-  SEQ ID NO: 8
     Gly)

P17: cyclo(Pro-Arg-Ile-Lys-Pro-His-  SEQ ID NO: 9
     Gln-Gly)

P19: cyclo(Gln-Ile-Met--Arg-Ile-Lys- SEQ ID NO: 10
     Pro-His-Gln-Gly-Gln-His-Ile-
     Gly-Glu)

P20: cyclo(DPhe-Pro-Gln-Ile-Met-Arg- SEQ ID NO: 11
     Ile-Lys-Pro-His-Gln-Gly-Gln-
     His-Ile-Gly)

P23: cyclo(DTyr-Pro-Arg-Ile-Lys-Pro- SEQ ID NO: 13
     His-Gln)

P24: cyclo(Giy-Arg-Ile-Lys-Pro-His)  SEQ ID NO: 25
```

and the cyclopeptides P11 and P20, wherein the DPhe is replaced by DTyr.]

[70. The system for activating angiogenesis according to claim 7, wherein the cyclopeptide is chosen from among the following cyclopeptides:

```
P11: cyclo(DPhe-Pro-Gln-Ile-Met-Arg- SEQ ID NO: 6
     Ile-Lys-Pro-His-Gln-Gly-Gln-
     His-Ile-Gly-Glu)

P16: cyclo(Arg-Ile-Lys-Pro-His-Gln-  SEQ ID NO: 8
     Gly)

P17: cyclo(Pro-Arg-Ile-Lys-Pro-His-  SEQ ID NO: 9
     Gln-Gly)

P19: cyclo(Gln-Ile-Met--Arg-Ile-Lys- SEQ ID NO: 10
     Pro-His-Gln-Gly-Gln-His-Ile-
     Gly-Glu)

P20: cyclo(DPhe-Pro-Gln-Ile-Met-Arg- SEQ ID NO: 11
     Ile-Lys-Pro-His-Gln-Gly-Gln-
     His-Ile-Gly)

P23: cyclo(DTyr-Pro-Arg-Ile-Lys-Pro- SEQ ID NO: 13
     His-Gln)

P24: cyclo(Gly-Arg-Ile-Lys-Pro-His)  SEQ ID NO: 25
```

and the cyclopeptides P11 and P20, wherein DPhe is replaced by DTyr.]

[71. The system for activating angiogenesis according to claim 8, wherein the cyclopeptide is chosen from among the following cyclopeptides:

```
P11: cyclo(DPhe-Pro-Gln-Ile-Met-Arg- SEQ ID NO: 6
     Ile-Lys-Pro-His-Gln-Gly-Gln-
     His-Ile-Gly-Glu)

P16: cyclo(Arg-Ile-Lys-Pro-His-Gln-  SEQ ID NO: 8
     Gly)

P17: cyclo(Pro-Arg-Ile-Lys-Pro-His-  SEQ ID NO: 9
     Gln-Gly)

P19: cyclo(Gln-Ile-Met--Arg-Ile-Lys- SEQ ID NO: 10
     Pro-His-Gln-Gly-Gln-His-Ile-
     Gly-Glu)

P20: cyclo(DPhe-Pro-Gln-Ile-Met-Arg- SEQ ID NO: 11
     Ile-Lys-Pro-His-Gln-Gly-Gln-
     His-Ile-Gly)

P23: cyclo(DTyr-Pro-Arg-Ile-Lys-Pro- SEQ ID NO: 13
     His-Gln)

P24: cyclo(Gly-Arg-Ile-Lys-Pro-His)  SEQ ID NO: 25
```

and the cyclopeptides P11 and P20, wherein DPhe is replaced by DTyr.]

[72. The system for activating angiogenesis according to claim 9, wherein the cyclopeptide is chosen from among the following cyclopeptides:

```
P11: cyclo(DPhe-Pro-Gln-Ile-Met-Arg- SEQ ID NO: 6
     Ile-Lys-Pro-His-Gln-Gly-Gln-
     His-Ile-Gly-Glu)

P16: cyclo(Arg-Ile-Lys-Pro-His-Gln-  SEQ ID NO: 13
     Gly)

P17: cyclo(Pro-Arg-Ile-Lys-Pro-His-  SEQ ID NO: 9
     Gln-Gly)

P19: cyclo(Gln-Ile-Met--Arg-Ile-Lys- SEQ ID NO: 10
     Pro-His-Gln-Gly-Gln-His-Ile-
     Gly-Glu)

P20: cyclo(DPhe-Pro-Gln-Ile-Met-Arg- SEQ ID NO: 11
     Ile-Lys-Pro-His-Gln-Gly-Gln-
     His-Ile-Gly)
```

-continued

P23: cyclo(DTyr-Pro-Arg-Ile-Lys-Pro- SEQ ID NO: 13
His-Gln)

P24: cyclo(Gly-Arg-Ile-Lys-Pro-His) SEQ ID NO: 25 and the cyclopeptides P11 and P20, wherein DPhe is replaced by DTyr.]

73. The method of preparing a system according to claim 57, which consists in subjecting a support made of organic polymer to irradiation by means of ionizing radiations, plasma, or photons onto defined zones of the support and then grafting the organic spacer arms onto said zones of the support.

74. The method of preparing a system according to claim 58, which consists in subjecting a support made of organic polymer to irradiation by means of ionizing radiations, plasma, or photons onto defined zones of the support and then grafting the organic spacer arms onto said zones of the support.

75. The method of preparing a system according to claim 59, which consists in subjecting a support made of organic polymer to irradiation by means of ionizing radiations, plasma, or photons onto defined zones of the support and then grafting the organic spacer arms onto said zones of the support.

76. The method of preparing a system according to claim 60, which consists in subjecting a support made of organic polymer to irradiation by means of ionizing radiations, plasma, or photons onto defined zones of the support and then grafting the organic spacer arms onto said zones of the support.

77. The method of preparing a system according to claim 61, which consists in subjecting a support made of organic polymer to irradiation by means of ionizing radiations, plasma, or photons onto defined zones of the support and then grafting the organic spacer arms onto said zones of the support.

78. The method of preparing a system according to claim 62, which consists in subjecting a support made of organic polymer to irradiation by means of ionizing radiations, plasma, or photons onto defined zones of the support and then grafting the organic spacer arms onto said zones of the support.

79. The method of preparing a system according to claim 63, which consists in subjecting a support made of organic polymer to irradiation by means of ionizing radiations, plasma, or photons onto defined zones of the support and then grafting the organic spacer arms onto said zones of the support.

80. The method of preparing a system according to claim 64, which consists in subjecting a support made of organic polymer to irradiation by means of ionizing radiations, plasma, or photons onto defined zones of the support and then grafting the organic spacer arms onto said zones of the support.

81. The method of preparing a system according to claim 65, which consists in subjecting a support made of organic polymer to irradiation by means of ionizing radiations, plasma, or photons onto defined zones of the support and then grafting the organic spacer arms onto said zones of the support.

82. The method of preparing a system according to claim 66, which consists in subjecting a support made of organic polymer to irradiation by means of ionizing radiations, plasma, or photons onto defined zones of the support and then grafting the organic spacer arms onto said zones of the support.

83. The method of preparing a system according to claim 67, which consists in subjecting a support made of organic polymer to irradiation by means of ionizing radiations, plasma, or photons onto defined zones of the support and then grafting the organic spacer arms onto said zones of the support.

84. The method of preparing a system according to claim 68, which consists in subjecting a support made of organic polymer to irradiation by means of ionizing radiations, plasma, or photons onto defined zones of the support and then grafting the organic spacer arms onto said zones of the support.

85. The method according to claim 73, wherein the irradiation is carried out through a mask.

86. The method according to claim 74, wherein the irradiation is carried out through a mask.

87. The method according to claim 75, wherein the irradiation is carried out through a mask.

88. The method according to claim 76, wherein the irradiation is carried out through a mask.

89. The method according to claim 77, wherein the irradiation is carried out through a mask.

90. The method according to claim 78, wherein the irradiation is carried out through a mask.

91. The method according to claim 79, wherein the irradiation is carried out through a mask.

92. The method according to claim 80, wherein the irradiation is carried out through a mask.

93. The method according to claim 81, wherein the irradiation is carried out through a mask.

94. The method according to claim 82, wherein the irradiation is carried out through a mask.

95. The method according to claim 83, wherein the irradiation is carried out through a mask.

96. The method according to claim 84, wherein the irradiation is carried out through a mask.

97. The method according to claim 73, wherein the ionizing radiations are a beam of electrons or fast heavy ions.

98. The method according to claim 74, wherein the ionizing radiations are a beam of electrons or fast heavy ions.

99. The method according to claim 75, wherein the ionizing radiations are a beam of electrons or fast heavy ions.

100. The method according to claim 76, wherein the ionizing radiations are a beam of electrons or fast heavy ions.

101. The method according to claim 77, wherein the ionizing radiations are a beam of electrons or fast heavy ions.

102. The method according to claim 78, wherein the ionizing radiations are a beam of electrons or fast heavy ions.

103. The method according to claim 79, wherein the ionizing radiations are a beam of electrons or fast heavy ions.

104. The method according to claim 80, wherein the ionizing radiations are a beam of electrons or fast heavy ions.

105. The method according to claim 81, wherein the ionizing radiations are a beam of electrons or fast heavy ions.

106. The method according to claim 82, wherein the ionizing radiations are a beam of electrons or fast heavy ions.

107. The method according to claim 83, wherein the ionizing radiations are a beam of electrons or fast heavy ions.

108. The method according to claim 84, wherein the ionizing radiations are a beam of electrons or fast heavy ions.

109. The method according to claim 73, wherein the cyclopeptides are attached on the organic spacer arms prior to grafting.

110. The method according to claim 74, wherein the cyclopeptides are attached on the organic spacer arms prior to grafting.

111. The method according to claim 75, wherein the cyclopeptides are attached on the organic spacer arms prior to grafting.

112. The method according to claim 76, wherein the cyclopeptides are attached on the organic spacer arms prior to grafting.

113. The method according to claim 77, wherein the cyclopeptides are attached on the organic spacer arms prior to grafting.

114. The method according to claim 78, wherein the cyclopeptides are attached on the organic spacer arms prior to grafting.

115. The method according to claim 79, wherein the cyclopeptides are attached on the organic spacer arms prior to grafting.

116. The method according to claim 80, wherein the cyclopeptides are attached on the organic spacer arms prior to grafting.

117. The method according to claim 81, wherein the cyclopeptides are attached on the organic spacer arms prior to grafting.

118. The method according to claim 82, wherein the cyclopeptides are attached on the organic spacer arms prior to grafting.

119. The method according to claim 83, wherein the cyclopeptides are attached on the organic spacer arms prior to grafting.

120. The method according to claim 84, wherein the cyclopeptides are attached an the organic spacer arms prior to grafting.

121. The method according to claim 73, which further comprises a step of fixation of the cyclopeptides on the organic spacer arms after grafting of same.

122. The method according to claim 74, which further comprises a step of fixation of the cyclopeptides on the organic spacer arms after grafting of same.

123. The method according to claim 75, which further comprises a step of fixation of the cyclopeptides on the organic spacer arms after grafting of same.

124. The method according to claim 76, which further comprises a step of fixation of the cyclopeptides on the organic spacer arms after grafting of same.

125. The method according to claim 77, which further comprises a step of fixation of the cyclopeptides on the organic spacer arms after grafting of same.

126. The method according to claim 78, which further comprises a step of fixation of the cyclopeptides on the organic spacer arms after grafting of same.

127. The method according to claim 79, which further comprises a step of fixation of the cyclopeptides on the organic spacer arms after grafting of same.

128. The method according to claim 80, which further comprises a step of fixation of the cyclopeptides on the organic spacer arms after grafting of same.

129. The method according to claim 81, which further comprises a step of fixation of the cyclopeptides on the organic spacer arms after grafting of same.

130. The method according to claim 82, which further comprises a step of fixation of the cyclopeptides on the organic spacer arms after grafting of same.

* * * * *